United States Patent
Ande et al.

(10) Patent No.: US 10,036,742 B2
(45) Date of Patent: Jul. 31, 2018

(54) TRANSGENIC MICE EXPRESSING Y114F MUTANT PROHIBITIN

(71) Applicant: University of Manitoba, Winnipeg (CA)

(72) Inventors: Sudharsana Rao Ande, Winnipeg (CA); Khanh Hoa Nguyen, Winnipeg (CA); Suresh Mishra, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 59 days.

(21) Appl. No.: 15/278,820

(22) Filed: Sep. 28, 2016

(65) Prior Publication Data

US 2017/0089888 A1    Mar. 30, 2017

Related U.S. Application Data

(60) Provisional application No. 62/234,336, filed on Sep. 29, 2015.

(51) Int. Cl.
*G01N 33/50* (2006.01)
*A01K 67/027* (2006.01)
*C07K 14/47* (2006.01)

(52) U.S. Cl.
CPC ..... *G01N 33/5088* (2013.01); *A01K 67/0275* (2013.01); *C07K 14/4702* (2013.01); *A01K 2217/05* (2013.01); *A01K 2217/052* (2013.01); *A01K 2227/105* (2013.01); *A01K 2267/0331* (2013.01); *C12N 2830/008* (2013.01); *G01N 2500/00* (2013.01)

(58) Field of Classification Search
CPC ........... G01N 33/5088; G01N 2500/00; A01K 67/0275; A01K 2217/05; A01K 2217/052; A01K 2267/0331; C07K 14/4702; C12N 2830/008
See application file for complete search history.

*Primary Examiner* — Thaian N Ton
(74) *Attorney, Agent, or Firm* — Michael R. Williams; Ryan W. Dupuis; Ade & Company Inc.

(57) ABSTRACT

The Mito-Ob obese mouse model overexpresses the mitochondrial protein prohibitin (PHB). Mito-Ob male mice develop insulin resistance in addition to obesity and they do not develop overt diabetes. It has been discovered that these mice also spontaneously develop nonalcoholic steatohepatitis (NASH) and hepatocarcinogenesis over time. Also described is a mutant Mito-Ob mouse that develops lymphadenopathy and histiocytosis.

4 Claims, 12 Drawing Sheets

SEQUENCE LISTING

<160> NUMBER OF SEQ ID NOS: 3

<210> SEQ ID NO 1
<211> LENGTH: 826
<212> TYPE: DNA
<213> ORGANISM: mouse

<400> SEQUENCE: 1

```
aaagggaaca aaagctggag ctccaccgcg gtggagctcg agtcagtgag cgaggaagcg     60
gaagagtcta gagtcgacca gacatgataa gatacattga tgagtttgga caaaccacaa    120
ctagaatgca gtgaaaaaaa tgctttattt gtgaaatttg tgatgctatt gctttatttg    180
taaccattat aagctgcaat aaacaagttc tgctttaata agatctgatt cgaattccaa    240
gcttggatcc gaattcgccc tatagtgagt cgtattacgc ggccgctcta gaactagtgg    300
atccccgggg ctgcagcaca ggagggtgct atgagcctct gaagtccaga tagctcactt    360
ttaaagatgc cctgaccatg tgactgtagg agtgaccaat gggggccaga tcatttcctt    420
catgaccaga ccctgtatgt tttcctctga gtcatgtttt taatagaaat ttctcaactt    480
tggttctccc tggcaatgat cactggactt agagtacaaa ttatttttaa ccatgaacag    540
agtattttaa aggttcctgt tttgactgtc aaaagctaat gcattgaact tccccccatt    600
attccttatg gatttgcctc attgtggagg agacaattat cttggacaca tttgaccttc    660
ttatcttgag ttttattttt attaatactg caataatgtg tttagttctt ctgaatttga    720
gaacataaaa actatcttag agattcttag tcttaatggc tcttttgtta gaatagtgtt    780
tatctcacga attttaacaa aataaataat gacattttaa agtagc                   826
```

<210> SEQ ID NO 2
<211> LENGTH: 272
<212> TYPE: PRT
<213> ORGANISM: mouse

<400> SEQUENCE: 2

Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
                20                  25                  30

Gly His Arg Ala Val Ile Phe Asp Arg Phe Arg Gly Val Gln Asp Ile
            35                  40                  45

Val Val Gly Glu Gly Thr His Phe Leu Ile Pro Trp Val Gln Lys Pro
        50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270

<210> SEQ ID NO 3
<211> LENGTH: 272
<212> TYPE: PRT
<213> ORGANISM: mouse

<400> SEQUENCE: 3

Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
                20                  25                  30

Gly His Arg Ala Val Ile Phe Asp Arg Phe Arg Gly Val Gln Asp Ile
            35                  40                  45

Val Val Gly Glu Gly Thr His Phe Leu Ile Pro Trp Val Gln Lys Pro
        50                  55                  60

```
Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
                100                 105                 110

Asp Phe Asp Glu Arg Val Leu Pro Ser Ile Thr Thr Glu Ile Leu Lys
            115                 120                 125

Ser Val Val Ala Arg Phe Asp Ala Gly Glu Leu Ile Thr Gln Arg Glu
    130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
            245                 250                 255

Ile Thr Tyr Leu Pro Ala Gly Gln Ser Val Leu Leu Gln Leu Pro Gln
                260                 265                 270
```

TRANSGENIC MICE EXPRESSING Y114F MUTANT PROHIBITIN

PRIOR APPLICATION INFORMATION

The instant application claims the benefit of U.S. Provisional Patent Application Ser. No. 62/234,336, filed Sep. 29, 2015 and entitled "USES OF MITO-OB TRANSGENIC MICE", the contents of which are incorporated herein by reference.

BACKGROUND OF THE INVENTION

Hepatocellular carcinoma (HCC) is the fifth most common cancer and a leading cause of cancer related death worldwide (Nakagawa et al., 2014, Cancer Cell. 26: 331-343). The pathogenesis of HCC has been mostly associated with cirrhosis due to chronic infection by hepatitis B virus and hepatitis C virus, as well as due to toxic injury from alcoholism (E I Seag, 2011, N Eng J Med 365: 118-127). While a substantial number of cases cannot be explained by these etiologies, HCC is increasingly diagnosed among obese individuals (Turati et al., 2913, Br J Cancer 108: 222-228). Obesity and obesity-related disorders such as non-alcoholic fatty liver disease (NAFLD), steatohepatitis, insulin resistance and type 2 diabetes exhibit an increased risk for developing HCC (Tilg et al., 2014, Best Pract Res Clin Gastroenterol 28:599-610). For instance, in a large prospective cohort of the Cancer Prevention Study in North American subjects, the relative risk of dying from liver cancer among men with a BMI≥35 $kg/m^2$ was 4.5 fold higher compared to a reference group with normal body weight (Calle et al., 2003, N Engl J Med 348: 1625-1638). Similarly, in a Swedish cohort study of men, the relative risk of HCC in individuals with a BMI≥30 $kg/m^2$ was 3.1 fold higher than in normal weight controls (Samanic et al., 2006, Cancer Causes Control 17: 901-909). Similar findings have been reported from other parts of the world (Wolk et al., 2001, Cancer Causes Cotrol 12: 13-21; Borena et al., 2012, Int J Cancer 131: 193-200; Schlesinger et al., 2013, Int J Cancer 132: 645-657). Obesity increases male HCC risk by 4-8 fold (Calle et al., 2004, Nat Rev Cancer 4: 579-591), and also increases HCC risk in viral hepatitis (Chen et al., 2008, Gastroenterology 135: 111-121). Furthermore, obesity associated tumors appear to be more aggressive, have an increased risk of recurrence, and result in higher mortality (Carmichael, 2006, BJOG 113: 1160-1166; Murphy et al., 2000, Am J Epidemiol 152: 847-854).

Hepatic manifestations of obesity and metabolic syndrome are collectively termed NAFLD, which is commonly associated with insulin resistance and hyperinsulinemia (Marchesini et al., 1999, Am J Epidemiol 152: 847-854). In general, NAFLD is apparently benign, but approximately 20% of all cases present as nonalcoholic steatohepatitis (NASH) featuring hepatocellular injury and inflammation, with a risk of progression to cirrhosis and HCC (Marrero et al., 2002, Hepatology 36: 1349-1354; Ekstedt et al., 2996, Hepatology 7: 234-238; Rafiq et al., 2007, Clin Gastroenterol Hepatol 7: 234-238). The overall public health impact of an association between NAFLD, NASH and HCC remains substantial considering high prevalence of obesity and related metabolic conditions worldwide. Emerging evidence suggest that NAFLD is associated with the development of non-cirrhotic HCC (Guzman et al., 2008, Arch Pathol Lab Med 132: 1761-1766; Paradis et al., 2009, Hepatology 42: 851-859; Ertle et al., 2010, Int J Cancer 128: 2436-2443). For example, in an analysis of the SEER-Medicare database identified a total of 17,895 cases of HCC of which 2,863 cases (16%) were due to biopsy-proven NAFLD without evidence for other etiologies (Rahman et al., 2012, Hepatology 56: 241A). Remarkably, a total of 1,031 cases (36%) of NAFLD-associated HCC were diagnosed in non-cirrhotic livers and 18% of these cases developed in isolated fatty liver without steatohepatitis (Rahman et al., 2012). This suggests that cirrhosis is not necessary for the development of HCC in obesity. Because of the epidemic proportions of obesity, there is an increasing probability that adverse metabolic conditions coexist with chronic liver disease, and obesity-associated abnormalities may enhance the effect of other established risk factors of HCC. Several studies support this notion such as alcoholic liver disease and chronic viral hepatitis associated HCC (Karagozian et al., 2014, Metabolism Clinical and Experimental 63: 607-617).

A number of molecular mechanisms have been linked to obesity and its associated abnormalities that may facilitate the development of HCC, such as adipose tissue inflammation, hepatic lipotoxicity, and insulin resistance (Karagozian et al., 2014). These and other pathological events in obesity have complex interactions while their relative contribution to the development of HCC in various stages of hepatic steatosis progression remains to be determined. Because of the continuous increase in obesity associated hepatic steatosis worldwide, there is an urgent need to better understand the underlying mechanism involved in obesity-linked HCC development. However, one major obstacle for the mechanistic study is the lack of suitable animal models that spontaneously develop obesity associated NAFLD, NASH and HCC in a progressive manner. For example, the majority of the studies investigating the impact of obesity on transgene or carcinogen-induced HCC development or progression have been done using diet-induced obese (DIO) models (Nakagawa et al., 2014; Umemura et al., 2014, Cell Metab 20: 133-144; Duan et al., 2014, BMC Gastroenterol 20: 195; Tajima et al., 2013, Am J Physiol Endocrinol Metab 305: E987-998). A major disadvantage of DIO model is that it is very difficult to discern the effect of diet from overweight/obesity and obesity from insulin resistance, which often coexist. Likewise, mechanisms involved in the development and progression of carcinogen-induced HCC may not apply to obesity-linked HCC in humans that develop progressively due to systemic changes in the body. Thus, suitable preclinical models that incorporate natural history estimates of disease progression are needed for a better understanding of the mechanisms of obesity-linked NASH and HCC. In addition, a suitable animal model is required for appropriate and meaningful intervention and preclinical studies.

Emerging evidence suggests that obesity is a risk factor for different types of cancer, and obesity at the time of cancer diagnosis is associated with poorer survival rates (Renehan et al., 2008, Lancet 371: 569-578; Wolin et al., 2010, Oncologist 5: 556-565). Furthermore, obese patients are at a greater risk of tumor recurrence and metastasis (Makarem et al., 2015, Cancer Causes Control 26: 277-286). The mechanisms underlying these associations are not understood, partly due to the lack of suitable animal models and the difficulties associated with human studies. Several hypotheses have been proposed to explain this association. One of them is centered on adipose tissue as an endocrine organ and obesity as an endocrine disorder with increased circulating levels of insulin, bioavailable IGF-I, estrogen, inflammatory cytokines and leptin (Hernandez et al., 2015, Cancer Med 10:375; Madeddu et al., J Cell Mol Med 18: 2519-2529; Rose et al., 2004, Obes Rev 5: 153-165). There is accumulating evidence suggesting that the metabolic effects of obesity through insulin resistance are risk factors for cancer development (DeCensi et al., 2014, Breast Cancer Res Treat 148: 81-90; Zhao et al., 2014, World J Clin Oncol 5: 248-262). This evidence is primarily derived from epidemiological studies indicating that patients with metabolic syndrome have a higher incidence of cancer (Renehan et al., 2006, Trends Endocrinol Metab 17: 328-336). In patients with insulin resistance, the reduced sensitivity of metabolic tissues to insulin results in elevated blood glucose and insulin levels. Chronic hyperinsulinemia promotes the secretion of IGF-I and reduces the production of IGF binding proteins, which in turn further increases bioavailable IGF-I (Gallagher et al., 2013, Diabetes 62: 3553-3560). Through the IGF-I receptor, IGF-I and/or insulin activate downstream signaling pathways that promote mitogenic and proangiogenic factors and inhibit apoptosis (Renehan et al., 2006; Gallagher et al., 2013). Insulin itself is mitogenic and antiapoptotic (Renehan et al., 2006). These mediators, along with their interacting partners and pathways, form the complex molecular network by which obesity impacts the pathological manifestation of carcinogenesis. However, it is not known how physiological factors like insulin, estrogen, leptin and IGF-I lead to cancer growth.

A number of studies have been done to address the connection between obesity and cancer, using common obese rodent models (Gallgher et al., 2013; Gahete et al., 2014, Carcinogenesis 35: 2467-2473; Hvid et al., 2013, PLoS One 8: 79710). In the majority of the studies, either genetically obese (e.g. ob/ob, db/db) or diet-induced obese rodent models have been used to investigate transgene and carcinogen-induced tumor development (Gahete et al., 2014; Hvid et al., 2013; Nakagawa et al., 2014). To study tumor progression, the major focus has been on allograft studies in mice with either genetic or diet-induced obesity (Hvid et al., 2013; Zhang et al., 2009, Cancer Res 69: 5259-5266). In general, obesity has been demonstrated to shorten tumor latency and to worsen tumor pathology. However, in genetic models with a defect in leptin or the leptin receptor, the impact of obesity is not as straightforward (Cleary, 2013, J Mammary Gland Biol Neoplasia 18: 333-343). Likewise, with diet-induced obese rodent models, it is difficult to discern the effect of diet from being overweight and other confounding factors. Thus, there is a lack of apt translational models to study the relationship between obesity, insulin resistance and cancer. Future studies clearly distinguishing the diet component from body weight and obesity from insulin resistance effects, will be important in continuing to understand the factors associated with the impact of body weight on cancer development and progression.

We have been interested in understanding the role and the regulation of cell compartment specific functions of a pleiotropic protein, prohibitin (PHB, also known as PHB1) (Ande et al., 2009, Biochem Biophys Acta 2009: 1372-1378; Ande et al., 2012, In J Obes (Lond) 36: 1236-1244; Ande et al., 2014, Diabetes 63: 3734-3741). PHB localizes to mitochondria and the plasma membrane where it has a cell compartment specific function (Nijtmans et al., 2002, Cell Mol Life Sci 59: 143-155; Sharma et al., 2004, PNAS 101: 17492-17497). In the mitochondria, PHB functions as a lipid and protein chaperone (Richter et al., 2014, Cell Metab 20: 158-171), whereas in association with the plasma membrane, PHB has a role in membrane receptor signaling (Kim et al., 2013, Science Signaling 6:292; Rajalingam et al., 2005, Nat Cell Biol 8: 837-843). We have reported that the phosphorylation of PHB protein at tyrosine-114 residue has a role in intrinsic down regulation of tyrosine kinase signaling (Ande et al., 2009), and others have confirmed its a role in immune signaling (Kim et al., 2013). Recently, we have discovered that PHB has a role in adipocyte differentiation (Ande et al., 2012).

SUMMARY OF THE INVENTION

According to a first aspect of the invention, there is provided a method of determining if a compound of interest reduces severity of non-alcoholic steatohepatitis comprising:

growing a transgenic mouse overexpressing the mitochondrial protein prohibitin (PHB) to approximately at least 3 months of age;

administering the compound of interest to the transgenic mouse; and determining if the compound of interest delays onset or reduces severity of non-alcoholic steatohepatitis. Specifically, the compound may reduce the severity of one or more symptoms associated with NASH, for example, reduction in fatigue, weight loss, and weakness; or a reduction in fat in the liver, inflammation or liver damage; or delay onset of NASH.

According to another aspect of the invention, there is provided a method of determining if a compound of interest reduces severity of hepatocellular carcinoma comprising:

growing a transgenic mouse overexpressing the mitochondrial protein prohibitin (PHB) to approximately at least 3 months of age;

administering the compound of interest to the transgenic mouse; and determining if the compound of interest delays onset or reduces severity of hepatocellular carcinoma. Specifically, the compound may reduce the number of tumors and/or the size of tumors and/or the delay the onset of hepatocellular carcinoma. The compound may also prevent the development of HCC.

According to yet another aspect of the invention, there is provided a transgenic mouse developing histiocytosis and lymphadenopathy as compared to a wild-type male mouse of the same strain and an exogenous nucleic acid construct that comprises a promoter operably linked to a gene encoding Y114F mutant prohibitin.

According to a still further aspect of the invention, there is provided a transgenic mouse comprising a transgene, said transgene comprising a polynucleotide encoding a mouse Y114F mutant prohibitin protein operably linked to at least a portion of a regulatory region of a mouse aP2 promoter, wherein said transgenic mouse develops histiocytosis or lymphoadenopathy compared to a wild type mouse of the same strain.

According to yet another aspect of the invention, there is provided a transgenic mouse whose genome comprises: a DNA transgene encoding Y114F mutant prohibitin.

According to a still further aspect of the invention, there is provided a mouse transgenic fertilized egg comprising an expression construct comprising (a) a nucleotide sequence encoding Y114F mutant prohibitin and (b) a transcription-regulating sequence operatively linked to the nucleotide sequence.

According to another aspect of the invention, there is provided an isolated totipotent mouse cell comprising an exogenous nucleic acid construct that comprises Y114F mutant prohibitin operably linked to a suitable promoter.

According to a still further aspect of the invention, there is provided a method of determining if a compound of interest reduces severity of histiocytosis comprising:

growing a transgenic mouse overexpressing the Y114F mutant prohibitin (PHB) to approximately at least 3 months of age;

administering the compound of interest to the transgenic mouse; and determining if the compound of interest delays onset or reduces severity of histiocytosis.

According to another aspect of the invention, there is provided a method of determining if a compound of interest reduces severity of lymphadenopathy comprising:

growing a transgenic mouse overexpressing the Y114F mutant prohibitin (PHB) to approximately at least 3 months of age;

administering the compound of interest to the transgenic mouse; and determining if the compound of interest delays onset or reduces severity of lymphadenopathy.

DESCRIPTION OF THE PREFERRED EMBODIMENTS

Figure 1:
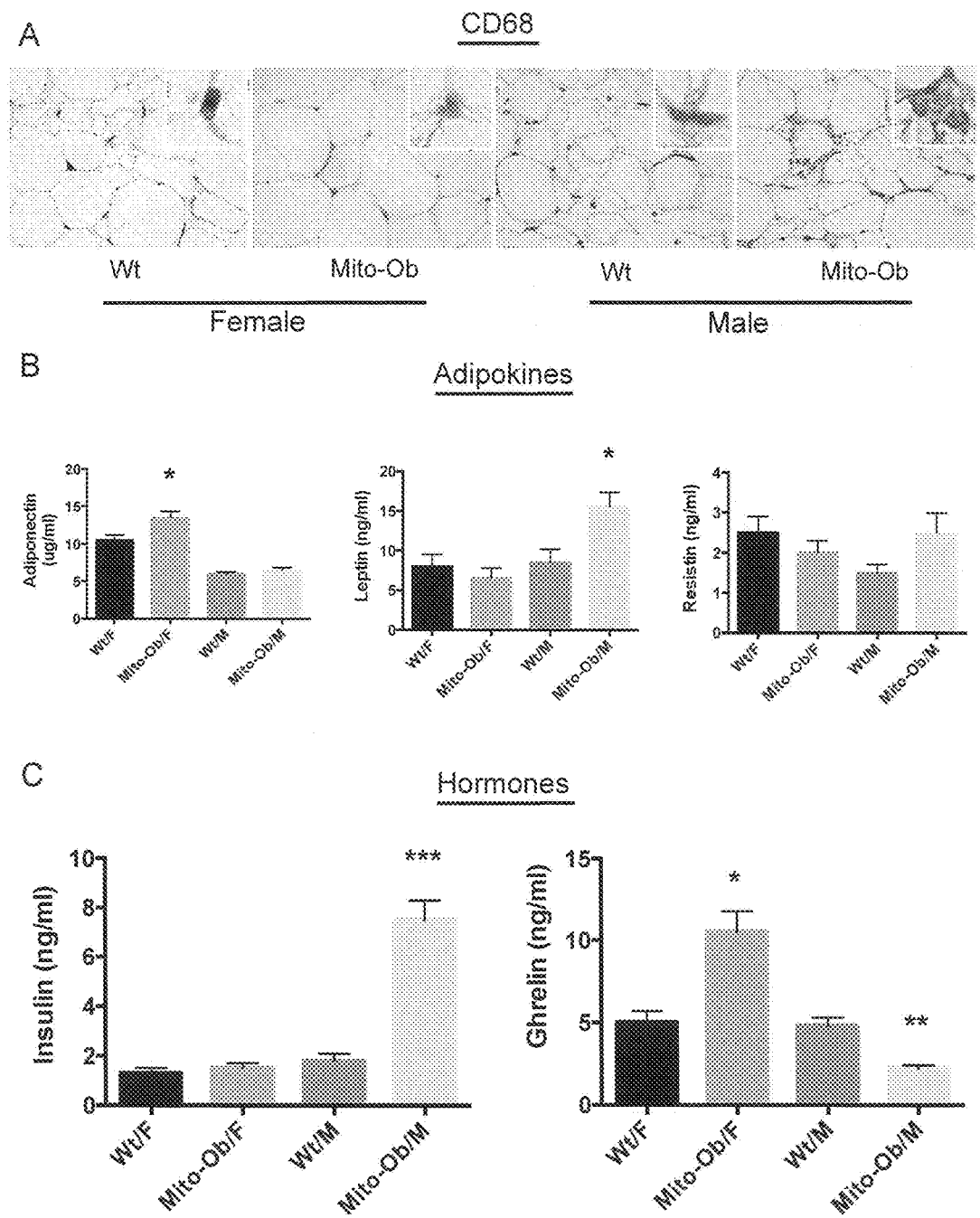
FIG. 1. Mito-Ob mice display sex differences in adipose tissue structure and function, and in metabolic dysregulation. (A) Representative photomicrographs showing immunohisto-chemical analysis of the inflammatory macrophages using anti-CD68 antibody in visceral adipose tissue from 9 months old Mito-Ob mice. Scale bars, 20 µm. (n=5-7 mice in each group). (B & C) Histograms showing serum adipokine and hormone levels in Mito-Ob mice at 9 months of age. Data are presented as mean±SEM (n=5-7 mice in each group). Asterisks indicate comparison between sex matched Mito-Ob vs Wt. NS, not significant; *P<0.05, P<0.01, *P<0.001 by Student's t test. Wt—wild type; F—female; M—male.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Published US Patent Application US 2015/0026833 teaches a transgenic mouse designated as Mito-Ob. Specifically, as discussed therein, the inventors developed an obese mouse model by overexpressing the mitochondrial protein prohibitin (PHB) in white adipose tissue (WAT) specific manner driven by adipocyte protein 2 (aP2) promoter. The inventors have named these mice "Mito-Ob" because they begin to develop obesity as a result of mitochondrial remodeling (upregulation of mitochondrial biogenesis and function) in WAT, thus are comparable to polygenic obese rodent models. The contents of this application are expressly incorporated herein by reference.

Mito-Ob male mice develop insulin resistance in addition to obesity and they do not develop overt diabetes. In this aspect, the Mito-Ob mice share similarities with a large portion of human obese population, the group who are both obese and insulin resistance but are not diabetic, as discussed below. The Mito-Ob mice therefore are a valuable animal model for obesity and metabolic syndrome.

Obesity increases the risk for nonalcoholic steatohepatitis (NASH) and hepatocarcinogenesis. However, the underlying mechanisms involved in the disease process remain unclear.

Surprisingly, with aging, the male Mito-Ob mice spontaneously develop obesity-linked NASH and hepatocellular carcinoma (HCC) progressively. In contrast, the female Mito-Ob mice maintained normal glucose and insulin levels and did not develop NASH and HCC. We believe this is to be the first report of a spontaneous and progressive preclinical model for obesity-linked NASH and HCC.

Intriguingly, an inverse alteration in the anti-inflammatory peptide ghrelin level was found between male and female Mito-Ob mice. Serum ghrelin was significantly upregulated in the female mice and down regulated in the male mice compared with respective control mice suggesting a potential role in sex-dimorphic phenotype in Mito-Ob mice. In addition, a marked reduction in the markers of mitochondrial content and function was found in the liver of male Mito-Ob mice with HCC development. Mechanistically, we found that ERK1/2 signaling was significantly upregulated whereas STAT3 signaling was significantly down regulated in the tumors from Mito-Ob mice. Akt signaling remains unchanged in the liver tumors compared with control liver. Collectively, these data demonstrate that metabolic and inflammatory status of the adipose tissue and their interplay at the systemic and hepatic level play a central role in the pathogenesis of obesity-linked NASH and HCC, and reveal a sex-dimorphic role of prohibitin in adipose and immune functions. A similar mechanism may underlie in obesity-linked NASH and HCC development in humans.

Provided herein is direct evidence for obesity associated hyperinsulinemia and chronic, low-grade inflammation in the development of NASH and HCC, independent of diet and carcinogen respectively. This pathological progression is marked by adipose inflammation, an inverse alteration in serum insulin and ghrelin levels, an increase in hepatic lipid accumulation, immune infiltration and a reduction in hepatic mitochondrial content and function, with a parallel increase in hepatic DNA damage, cell death and compensatory proliferation. Of note, both female and male Mito-Ob mice have comparable degrees of obesity; however, only males displayed pathological features of NASH and HCC. This would suggest that obesity per se is not sufficient for the development of NASH and HCC but rather adipose inflammation, hyperinsulinemia and the degree of systemic as well as hepatic inflammation are important. Collectively, the data indicates an extensive interplay between metabolic and inflammatory status at the adipose tissue and systemic levels, as well as at the hepatic tissue level in the progression of obesity-linked hepatic steatosis to HCC. This clearly indicates that obesity associated metabolic and immune dysregulation have a central role in the pathogenesis of NASH and HCC.

In this context, it is important to note that there are a number of obese rodent models available that display obesity associated metabolic dysregulation and NAFLD, but none of them develop HCC spontaneously. This raises the question of how and why obesity associated abnormalities lead to HCC development in the male Mito-Ob mice. This may in part be due to a significant reduction in ghrelin level in the male Mito-Ob mice because emerging evidences suggest that ghrelin is an important anti-inflammatory peptide (Batar et al, 2011, Mol Cell Endocrinol 340: 44-58; Kizaki et al., 2011, Biochem Biophys Res Commun 413: 454-459; Barazzoni et al., 2014, Obesity 22: 170-177; Li et al., 2013, Endocrine 43:376-386). Since obesity associated chronic low-grade inflammation in major metabolic tissues is considered as an important driver for obesity associated disorders, it is possible that the anti-inflammatory function of ghrelin has a role in the sexually dimorphic metabolic phenotype in Mito-Ob mice. Reduced ghrelin level in male Mito-Ob mice may be permissive for the development of obesity-associated low-grade inflammation, which in turn promotes insulin resistance, NASH and HCC. By the same token, increased ghrelin level in female Mito-Ob mice may have a protective role against obesity-associated low-grade inflammation, and subsequently from insulin resistance and fatty liver.

Moreover, we speculate that reduced ghrelin level in male Mito-Ob mice may be a direct effect of PHB overexpression in macrophages because the aP2 gene promoter used to generate Mito-Ob mice is also express in macrophages (Fu et al., 2006, Atherosclerosis 188: 102-111), which is known to produce ghrelin (Kizaki et al., 2011). It is possible that sex differences in ghrelin levels in Mito-Ob mice may be due to sex-dimorphic effect of PHB on ghrelin production from macrophages, which contribute to the development of NASH and HCC in male Mita-Ob mice and confer a protection in female mice. We propose that PHB overexpressing adipocytes and macrophages respond differently in males and females, especially in obesity, and that have a role in sex differences in metabolic dysregulation and adipose inflammation, and consequently in sex-dimorphic NASH and HCC development in male Mito-Ob mice.

Of note, insulin sensitizer such as thiazolidinediones (TZDs), glucagon-like peptide-1 receptor agonists and dipeptidyl peptidase 4 inhibitors have been studied as therapeutic approaches for NAFLD in recent years and have been shown to have some beneficial effects (Traussnigg et al., 2015, Dig Dis 33: 598-607). In addition, treatment with anti-inflammatory peptide ghrelin has been reported to reduce inflammation and oxidative stress NAFLD and NASH (Barazzoni et al., 2014; Li et al., 2013). Thus, a combination therapy of insulin sensitizers and anti-inflammatory agents especially ghrelin may provide a better outcome, as discussed below. The male Mito-Ob mouse is a fitting model for such preclinical studies because they display both pathological features that is insulin resistance and significantly reduced serum ghrelin levels.

The data suggest an important role of oncogenic determinant p-ERK in combination with mitochondrial dysregulation and p-STAT3 down regulation in the development of HCC in male Mito-Ob mice. Whether these changes are related to each other or work independently in HCC development remains to be determined. Glucotoxicity, lipotoxicity, and low-grade inflammation are known to cause mitochondrial dysregulation (Rossignol et al., 2014, Front Physiol 5: 150). In addition, p-STAT3 has recently been shown to play an important role in the maintenance of mitochondrial function (Han et al., 2014, Cell Signal 26: 2086-2095). A parallel change in mitochondrial dysregulation and p-STAT3 level during HCC development in male Mito-Ob mice would imply their coordination in the development of HCC that warrants further investigation. In this context, it is important to note that liver specific Phb knockout (Phb-/-) mice have been reported earlier, which also develop HCC by 35-46 weeks of age (Ko et al., 2010, Hepatology 52: 2096-2108). HCC development in Phb-/- mice has been attributed to the tumor suppressor function of Phb (Ko et al., 2010). However, because Phb is a critical protein for the structural and functional integrity of mitochondria, and hepatic mitochondrial dysregulation has been associated with HCC development (Koliaki et al., 2015, Cell Metabol 21: 739-746), it is possible that HCC development in Phb-/- mice may in part be due to compromised mitochondrial function.

This study benefits from a well-characterized transgenic obese mouse model with a sex-neutral obese phenotype but sex-dimorphic metabolic dysregulation that allows conclusion on a causal relationship between metabolic and immune dysregulation at the adipose tissue, systemic and hepatic levels in obesity-linked NASH and HCC development. In addition, the Mito-Ob mouse revealed a sex dimorphic role of prohibitin in adipose and immune functions.

As discussed herein, the Mito-Ob mice spontaneously develop the entire spectrum of obesity-NAFLD-NASH-HCC in a timely fashion with relatively larger window period between each successive stage during the disease process. Specifically, the mice develop obesity by approximately 3 months of age, insulin resistance and NAFLD by approximately 6 months of age, NASH by approximately 9 months of age and HCC by approximately 12 months of age.

Such rodent models are considered valuable because of increased potential for mechanistic underpinning, for the discovery of new therapeutic targets, and for preclinical intervention studies, as discussed below. Currently, a spontaneous and progressive preclinical model for obesity-linked NASH and HCC is not available. Thus, Mito-Ob mice have created a unique opportunity for mechanistic study of the disease process including sex differences in HCC prevalence, independent of diet and carcinogens, which is not possible with current approaches and models used. Mito-Ob mice will prove a valuable tool in advancing our understanding of NASH and HCC, because pathological features of the male Mito-Ob mice closely resemble steatohepatitic HCC features in humans.

As will be appreciated by one of skill in the art, low-grade inflammation is an integral component in the entire spectrum of obesity-related NAFLD-NASH-HCC progression. Consequently, Mito-Ob mice provide a unique opportunity to identify the earliest and best possible intervention/treatment for obesity-associated liver diseases. Such intervention may include targeting low-grade inflammation alone or in combination with insulin resistance at the different time points during the disease process, as discussed below. For example, while not wanting to be bound or limited to a particular hypothesis, it is possible that anti-inflammatory compound may work at all stages during the disease process (depending on dosage) whereas simultaneous treatment of insulin resistance and improving insulin sensitivity may provide additional benefit in the treatment outcome. It is also possible that targeting insulin resistance alone at the early stage may prevent disease progression. It is also possible that other compounds unrelated to insulin and/or inflammation may prove to be useful treatments for NASH/HCC.

As will be apparent to those of skill in the art, NAFLD, although more prevalent in humans than NASH or HCC, is generally considered benign and to be treatable by life style intervention. Furthermore, while NASH and HCC are related, the incidence of NASH is much higher than HCC. In other words, only 10-15% NASH cases will progress to HCC. Moreover, NASH alone without HCC can be equally devastating when the disease progresses to fibrosis/cirrhosis.

However, because Mito-Ob mice display spontaneous progression of NASH to HCC (unlike other models which may require exposure to a carcinogen), there is an added benefit of targeting HCC too, as discussed herein.

According to an aspect of the invention, there is provided a method of determining if a compound of interest reduces severity of non-alcoholic steatohepatitis comprising:

growing a transgenic mouse overexpressing the mitochondrial protein prohibitin (PHB) to approximately at least 3 months of age;

administering the compound of interest to the transgenic mouse; and determining if the compound of interest delays onset or reduces severity of non-alcoholic steatohepatitis. Specifically, the compound may reduce the severity of one or more symptoms associated with NASH, for example, reduction in fatigue, weight loss, and weakness; or a reduction in fat in the liver, inflammation or liver damage; or delay onset of NASH. That is, the compound of interest may delay the onset of NASH past 9 months. Alternatively, the compound may or may also delay the onset NAFLD past 6 months.

It is of note that this may be determined by comparison with an untreated or mock treated control. Furthermore, it is of note that the control does not necessarily need to be repeated for each compound.

As will be appreciated by one of skill in the art, the compound may be administered according to a regimen, for example, on a dosage regimen. For example, the compound of interest may be administered daily, for example, once per day or multiple times each day, for example, at feeding, or the compound may be administered every other day, two out of three days or on other similar regimens known to those of skill in the art. Furthermore, as will be appreciated by one of skill in the art, administration of the compound does not necessarily need to begin at 3 months of age, but may be delayed for example until shortly before the onset of NAFLD, at the onset of NAFLD, shortly after the onset of NAFLD, shortly prior to the onset of NASH, at the onset of NASH or shortly after the onset of NASH. In this manner, compounds can be tested for efficacy at different stages of disease progression. In this manner, for example, treatments for late stages of NAFLD and/or early onset of NASH may be developed.

As discussed above, the compound may be a compound known to have or suspected of having anti-inflammation properties and/or be a compound known or suspected to target insulin resistance. Alternatively, the compound may be a compound not specifically known or suspected of having these properties and/or may be a compound that has no known or suspected properties. Preferably, the compound of interest is administered in an amount that is believed to be or anticipated to be sufficient such that an known or suspected or theoretical properties of the compound of interest would be observed.

According to an aspect of the invention, there is provided a method of determining if a compound of interest reduces severity of hepatocellular carcinoma comprising:

growing a transgenic mouse overexpressing the mitochondrial protein prohibitin (PHB) to approximately at least 3 months of age;

administering the compound of interest to the transgenic mouse; and determining if the compound of interest delays onset or reduces severity of hepatocellular carcinoma. Specifically, the compound may reduce the number of tumors and/or the size of tumors and/or the onset of hepatocellular carcinoma. The compound may also prevent the development of HCC.

It is of note that this may be determined by comparison with an untreated or mock treated control. Furthermore, it is of note that the control does not necessarily need to be repeated for each compound.

The compound of interest may delay the onset of HCC past 12 months. The compound of interest may also delay onset of NASH past 9 months. Alternatively, the compound may or may also delay the onset NAFLD past 6 months.

As will be appreciated by one of skill in the art, the compound may be administered according to a regimen.

Furthermore, as will be appreciated by one of skill in the art, administration of the compound does not necessarily need to begin at 3 months of age, but may be delayed for example until shortly before the onset of NAFLD, at the onset of NAFLD, shortly after the onset of NAFLD, shortly prior to the onset of NASH, at the onset of NASH, shortly after the onset of NASH, shortly before the onset of HCC, or shortly after the onset of HCC. In this manner, compounds can be tested for efficacy at different stages of disease progression. In this manner, for example, treatments for late stages of NAFLD and/or early stages of NASH and/or early stages of HCC may be developed.

As discussed above, the compound may be a compound known to have or suspected of having anti-inflammation properties and/or be a compound known or suspected to target insulin resistance. Alternatively, the compound may be a compound not specifically known or suspected of having these properties and/or may be a compound that has no known or suspected properties.

In some embodiments, the expression of PHB is driven by adipocyte protein 2 (aP2) promoter. The aP2 promoter may comprise the nucleotide sequence as set forth in SEQ ID No:1:

```
pBS-aP2 promoter
                                                        (SEQ ID NO: 1)
AAAGGGAACA AAAGCTGGAG CTCCACCGCG GTGGAGCTCG AGTCAGTGAG

CGAGGAAGCG GAAGAGTCTA GAGTCGACCA GACATGATAA GATACATTGA

TGAGTTTGGA CAAACCACAA CTAGAATGCA GTGAAAAAAA TGCTTTATTT

GTGAAATTTG TGATGCTATT GCTTTATTTG TAACCATTAT AAGCTGCAAT

AAACAAGTTC TGCTTTAATA AGATCTGATT CGAATTCCAA GCTTGGATCC

GAATTCGCCC TATAGTGAGT CGTATTACGC GGCCGCTCTA GAACTAGTGG

ATCCCCCGGG CTGCAGCACA GGAGGGTGCT ATGAGCCTCT GAAGTCCAGA
```

```
                              -continued
TAGCTCACTT TTAAAGATGC CCTGACCATG TGACTGTAGG AGTGACCAAT

GGGGGCCAGA TCATTTCCTT CATGACCAGA CCCTGTATGT TTTCCTCTGA

GTCATGTTTT TAATAGAAAT TTCTCAACTT TGGTTCTCCC TGGCAATGAT

CACTGGACTT AGAGTACAAA TTATTTTAA CCATGAACAG AGTATTTAA

AGGTTCCTGT TTTGACTGTC AAAAGCTAAT GCATTGAACT TCCOCCCATT

ATTCCTTATG GATTTGCCTC ATTGTGGAGG AGACAATTAT CTTGGACACA

TTTGACCTTC TTATCTTGAG TTTTTATTTT ATTAATACTG CAATAATGTG

TTTAGTTCTT CTGAATTTGA GAACATAAAA ACTATCTTAG AGATTCTTAG

TCTTAATGGC TCTTTTGTTA GAATAGTGTT TATCTCACGA ATTTTAACAA

AATAAATAAT GACATTTTAA AGTAGC                              826
```

Preferably the prohibitin gene comprises the amino acid sequence as set forth in SEQ ID No:2.

```
Amino acid sequence for PHB
                                          SEQ ID No: 2
  1    MAAKVFESIG KFGLALAVAG GVVNSALYNV DAGHRAVIFD

41    RFRGVQDIVV GEGTHFLIPW VQKPIIFDCR SRPRNVPVIT

81    GSKDLQNVNI TLRILFRPVA SQLPRIFTSI GEDYDERVLP

121    SITTEILKSV VARFDAGELI TQRELVSRQV SDDLTERAAT

161    FGLILDDVSL THLTFGKEFT EAVEAKQVAQ QEAERARFVV

201    EKAEQQKKAA IISAEGDSKA AELIANSLAT AGDGLIELRK

241    LEAAEDIAYQ LSRSRNITYL PAGQSVLLQL PQ
```

A critical unmet need for the study of obesity-linked cancer is the lack of preclinical models that spontaneously develop obesity and cancer sequentially. As discussed herein, prohibitin (PHB) is a pleiotropic protein that has a role in adipose and immune functions. We capitalized on this attribute of PHB to develop a mouse model for obesity-linked tumor. We achieved this by expressing Y114F-PHB (m-PHB) from the aP2 gene promoter, for simultaneous manipulation of adipogenic and immune signaling functions. The m-PHB mice develop obesity in a sex-neutral manner but only male mice develop hyperinsulinemia. Consequently, male m-PHB mice develop histiocytosis with lymphadenopathy. The data demonstrates that obesity-associated hyperinsulinemia promotes tumor development by facilitating dormant mutant to manifest and reveals a sex-dimorphic role of PHB in adipose-immune interaction or immunometabolism.

We hypothesized that simultaneous manipulation of mitochondria associated adipogenic function and the loss of tyrosine-114 dependent cell signaling function of PHB will lead to obesity-linked tumor development. To test this hypothesis, we developed a second transgenic obese mouse model (m-Mito-Ob) overexpressing Y114F-phospho-mutant form of PHB (m-PHB) under the control of adipocyte protein-2 (aP2) promoter, for simultaneous manipulation of the pleiotropic functions of PHB in adipocytes and macrophages, because aP2 is expressed in both cell types (Fu et al., 2006, Atherosclerosis 188: 102-111; Kusminski et al., 2012, Nat Med 18: 1539-1549). Here we report a spontaneous and progressive preclinical model for obesity-linked tumor and reveal a sex-dimorphic role of PHB in adipose-immune interaction or immunometabolism.

The metabolic and immunological processes are associated with each other and they often undergo parallel changes in normal physiology, during aging and in various diseases. For instance, during pregnancy, the metabolic and immunological status of the mother undergoes significant changes in favor of the developing fetus (Markle et al., 2014 Trends in Immuno 35: 97-104). Likewise, parallel alterations in metabolic and immunological processes occur in the development and progression of obesity and some cancer (Dixit, 2008, J Leukocyte Biol 84: 882-892; Dixit et al., 2004, J Clin Invest 114: 57-66). Emerging evidence suggest that obesity affects the immune system and increases inflammatory macrophages, and that obesity-induced inflammation potentially promotes a variety of diseases including type 2 diabetes and cancer (Mathis et al., 2011, Nat Rev Immunology 11: 81-83). The focus has been on direct interactions between adipocytes and immune cells by cell-cell contact and via their secreted products such as adipokines and cytokines respectively (Sell et al., 2012, Nat Rev Endocrinol 8: 709-716). However, our understanding of proteins and signals that work upstream in the early event in their crosstalk in adipocyte and macrophage specific manner is limited. In particular, a potential role of a pleiotropic protein, with adipocyte and macrophage specific function, in their crosstalk has not been explored. Study of such proteins may provide new insights in the disease process and a rationale for simultaneous targeting of metabolic and immunological processes in various diseases.

Here we describe a spontaneous and progressive, sex-neutral transgenic obese mouse model, with sex-dimorphic phenotype of obesity-associated insulin resistance and insulin resistance-linked tumor, and report that PHB has a role in adipose-immune interaction. We believe this is to be the first report demonstrating the role of a pleiotropic protein with adipocyte and macrophage specific function in adipose-immune interactions in a sex-dimorphic manner. The development of histiocytosis only in male m-Mito-Ob is consistent with its male predominance in humans (Roding et al., in Diagnostic Histopathology of Tumors, 4th Edition, Fletcher (Ed), 2013). Our data suggests a potential role of sex steroids and ghrelin in the modulation of the crosstalk between metabolic and immunological processes in m-Mito-Ob mice in a sex dimorphic manner. The tumor development only in the male m-Mito-Ob and not in the male Mito-Ob mice despite similar metabolic status provides evidence that obesity associated abnormalities facilitate cancer development by promoting the manifestation of preexisting dormant mutant that would not manifest otherwise. Our data provides a rationale for identifying somatic dormant mutations that may manifest under obesity-associated abnormalities and have a role in obesity-linked cancer development in humans.

Histiocytoses are disorders caused by dysregulated proliferation or activation of macrophages or dendritic cells (Leenen et al., 2010, J Leukocyte Biol 87: 949-958). The pathogenesis of the most of these diseases is poorly understood, partially because of the lack of suitable animal models (Leenen et al., 2010). For instance, a spontaneous and progressive rodent model for histiocytosis with lymphadenopathy has not been reported. There are only a few animal models for this disease and they are developed either by virus-mediated transformation or cell transplantation in humanized mice (Nikolic et al., 2005, in Hitiocytic Disorders of Children and Adults (Weitzman et al., eds); Pileri et al., 2002, Histopathology 41: 1-29; De Gruijl et al., 2006, J Immunol 176: 7232-7242). Since the establishment of mouse models, it has become increasingly apparent that macrophages and dendritic cells comprise a very heterogeneous population of cells with overlapping origins, phenotypes, and functions (Nikolic et al., 2005; Pileri et al., 2002; De Gruijl et al., 2006). The overlapping immunohistological phenotype of macrophages and dendritic cells as observed in this study is consistent with the available literature in this context. Similar phenotypic switches between macrophages and dendritic cells have been observed in other systems (Nikolic et al., 2005; De Gruijl et al., 2006). In addition, occurrence of similar cases has been described in tumors of macrophages and dendritic cells in humans that showed characteristics of histiocytic sarcoma and dendritic cell malignancy (Pileri et al., 2002). Moreover, the lack of histiocytes proliferation in spleen and liver would indicate that adaptation of phenotype depended on the target organ in which the cells homed and proliferated.

Sex dimorphic differences in adipokines, chemokines, cytokines, and hormones in male and female m-Mito-Ob would suggest that PHB has sex dimorphic effects on adipocytes and macrophages, and this may be the reason behind obesity and inflammation induced insulin resistance only in male m-Mito-Ob mice. Of note, ghrelin has emerged as a potent anti-inflammatory hormone (Dixit et al., 2004; Dixit et al., 2006, Brain Behav Immun 20: 14; Gonzalez-Rey et al., 2006, Gastroenterology 130: 170-1720; Li et al., 2004, Circulation 109: 2221-2226), and reduction in ghrelin levels is associated with increased inflammation during obesity (Wiedmer et al., 2007, Clin Pract Endocrinol Metab 3: 705-712). Significantly increased ghrelin levels in the female m-Mito-Ob along with augmented immune response, as reflected by altered cytokine levels, may have a role in protection from obesity associated insulin resistance and tumor development, unlike male m-Mito-Ob mice. By the same token, significantly reduced ghrelin level along with attenuated immune response and increased chemokine (SDF-1, CCL21 and GCP-2) levels in male m-Mito-Ob mice may be responsible for male-specific metabolic dysregulation and tumor development through recruitment of macrophages and lymphocytes to the adipose tissue and lymph nodes. Our findings are consistent with the emerging notion that ghrelin is a potent anti-inflammatory peptide and may be a key player in adipose-immune interactions.

In addition to the involvement of immunological processes in obesity-associated abnormalities and chronic diseases, it has a role in increasing longevity under caloric restriction (Takahashi et al., 2011, Biochem Biophys Res Commun 405: 462-467). The exact cellular and molecular mediators responsible for integrating these two extreme metabolic states of obesity and caloric restriction to immune function are beginning to be elucidated. Emerging evidence suggests that ghrelin has a role in promoting longevity under caloric restriction (Markle et al., 2014). In this context it is important to note that PHB promotes longevity in Caenorhabditis elegans depending on metabolic status and genetic background (Arta;-Sanz et al., 2009, Nature 461: 793-797); and it has been identified as a candidate protein under mild caloric restriction induced longevity in mammals (Takahashi et al., 2011, Biochem Biophys Res Commun 405: 462-467). A parallel sex-dimorphic change in ghrelin levels and metabolic-immune phenotype in m-Mito-Ob mice would suggest a link between ghrelin and PHB in integrating metabolic and immune functions.

An important finding of this study is sex-dimorphic phenotype of m-Mito-Ob mice in the development of insulin resistance and tumors in male sex-specific manner despite the fact that m-Mito-Ob mice develop obesity in a sex-neutral manner. Notably, m-Mito-Ob mice start to gain weight during puberty when sex hormone levels begin to rise. This would suggest that PHB might require sex steroids for the manifestation of obese phenotype in m-Mito-Ob mice or sex steroids modulate PHB function in adipose tissue (Ande et al., 2014). In addition, the metabolic phenotype of m-Mito-Ob would suggest that adipocytes and macrophages expressing m-PHB respond differently in male and female under overweight or obese condition, and sex steroids may have a role in this process as sex dimorphism exists in various aspects of adipose and immune functions (Markle et al., 2014). Taken together, these results suggest that whole body metabolic status has a role in the modulation of macrophage effector function, and in the development of obesity-linked histiocytosis with lymphadenopathy in m-Mito-Ob mice. Thus, Mita-Ob and m-Mito-Ob mice provide a unique opportunity to investigate the effects of low-grade inflammation on tissues that regulate whole-body metabolism, such as adipose tissue and liver, and to explore the role of metabolic changes within immune cells on inflammatory phenotype. Collectively, our data suggest that the crosstalk between systemic metabolic status and inflammatory status of macrophages has an important role in translating pathogenic effects of obesity, and the interplay between sex steroids, ghrelin and PHB have a role in this process in m-Mito-Ob mice (FIG. 12).

Figure 12:
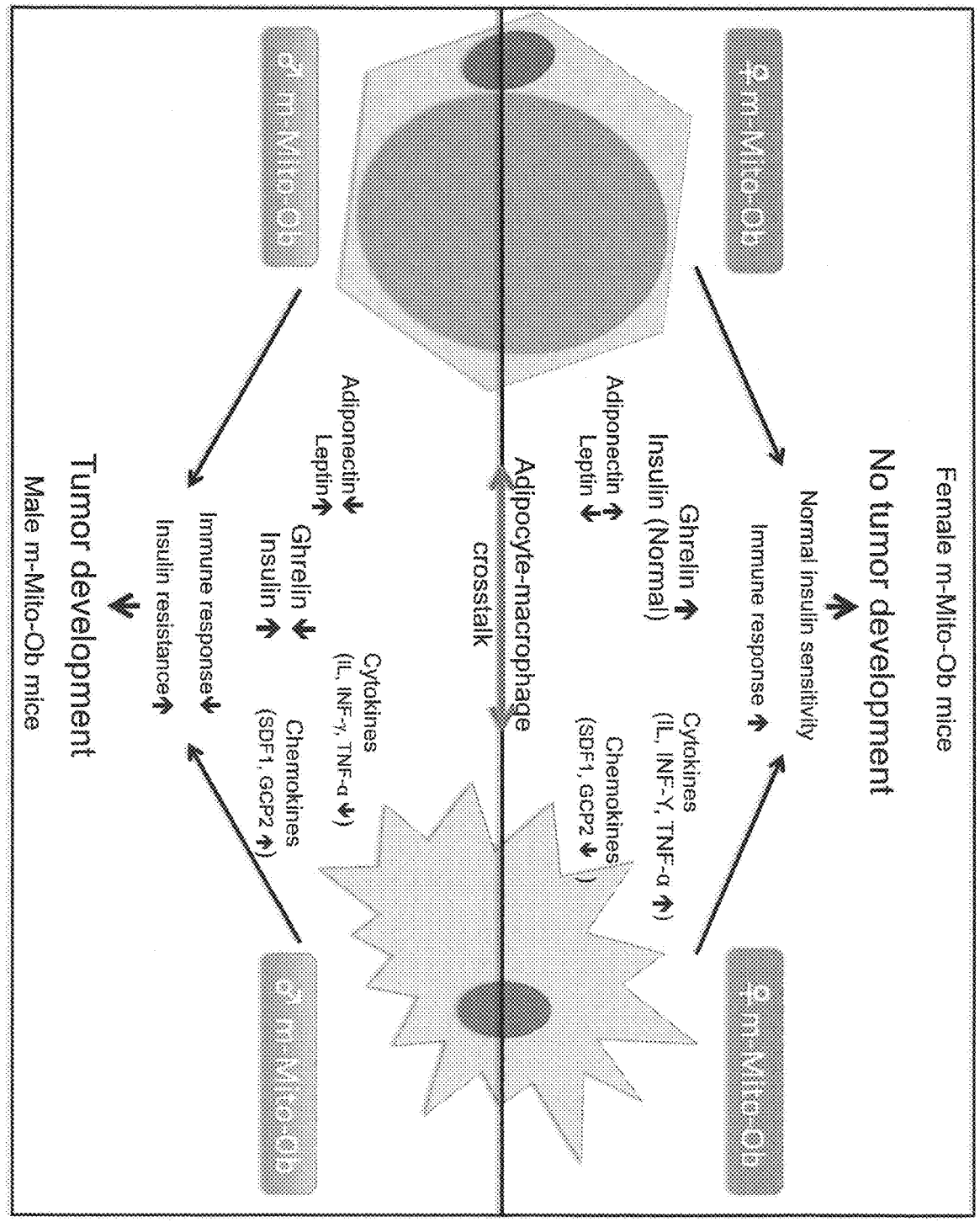
FIG. 12. Schematic diagram depicting the effect of various factors in sex-dimorphic metabolic dysregulation and tumor development in the male m-Mito-Ob mice. Adipocytes and macrophages expressing m-PHB respond differently in female and male m-Mito-Ob mice resulting in altered adipose-immune interaction, which in turn leads to sex-dimorphic metabolic phenotype and consequently tumor development in male m-Mito-Ob mice.

As discussed herein, we provide evidence that obesity-associated hyperinsulinemia promotes cancer development by facilitating dormant mutant to manifest and reveal a sex dimorphic role of PHB in adipose-immune crosstalk (FIG. 12). Our data indicate a role for PHB in integrating the role of sex steroids and ghrelin in adipose-immune interactions (FIG. 12). Our discovery of PHB as an important protein in adipose-immune interactions is a step towards mechanistic underpinnings of metabolic-immune crosstalk. Targeting PHB may provide a unique opportunity for the modulation of immunometabolism in obesity, cancer and in immune diseases. Mito-Ob and m-Mito-Ob mice together prove valuable tools in elucidating the mechanisms involved in the interplay between metabolic and immunological processes in health and diseases.

Similar to the Mito-Ob mice, the m-Mito-Ob mice also develop obesity by approximately 3 months of age, insulin resistance/hyperinsulinemia by approximately 6 months of age and lymph node tumors by approximately 9 months of age.

As discussed herein, the inventors have developed an obese mouse model by overexpressing the mitochondrial protein Y114F mutant prohibitin in adipocyte and macrophage specific manner driven by adipocyte protein 2 (aP2)

promoter. As discussed above, the male mice develop histiocytosis and lymphadenopathy.

According to an aspect of the invention, there is provided a transgenic mouse developing histiocytosis and lymphadenopathy as compared to a wild-type male mouse of the same strain and an exogenous nucleic acid construct that comprises a promoter operably linked to a gene encoding Y114F mutant prohibitin.

As discussed below, preferably the Y114F mutant prohibitin gene comprises the amino acid sequence as set forth in SEQ ID No:3.

The promoter may be adipocyte protein 2 (aP2) promoter and the aP2 promoter may comprise the nucleotide sequence as set forth in SEQ ID No:1.

The exogenous nucleic acid construct may be integrated into the mouse genome.

According to another aspect of the invention, there is provided a transgenic mouse, comprising a transgene, said transgene comprising a polynucleotide encoding a mouse Y114F mutant prohibitin protein operably linked to at least a portion of a regulatory region of a mouse aP2 promoter, wherein said transgenic mouse develops histiocytosis or lymphoadenopathy compared to a wild type mouse of the same strain.

Preferably, the transgenic mouse is a male transgenic mouse.

Preferably, the Y114F mutant prohibitin protein comprises an amino acid sequence as set forth in SEQ ID No:3.

```
Amino acid sequence for mutant PHB [Y114F-PHB]
                                       (SEQ ID NO: 3)
  1    MAAKVFESIG KFGLALAVAG GVVNSALYNV DAGHRAVIFD

41    RFRGVQDIVV GEGTHFLIPW VQKPIIFDCR SRPRNVPVIT

81    GSKDLQNVNI TLRILFRPVA SQLPRIFTSI GEDFDERVLP

121    SITTEILKSV VAREDAGELI TQRELVSRQV SDDLTERAAT

161    FGLILDDVSL THLTFGKEFT EAVEAKQVAQ QEAERARFVV

201    EKAEQQKKAA IISAEGDSKA AELIANSLAT AGDGLIELRK

241    LEAAEDIAYQ LSRSRNITYL PAGQSVLLQL PQ
```

Preferably, the aP2 promoter comprises the nucleotide sequence as set forth in SEQ ID No:1.

The transgene may be integrated into the mouse genome.

According to another aspect of the invention, there is provided a transgenic mouse whose genome comprises: a DNA transgene encoding Y114F mutant prohibitin.

The prohibitin may be encoded the nucleic acid sequence deduced from the amino acid sequence as set forth in SEQ ID No:3.

The transgene may be operably linked to aP2 promoter and the aP2 promoter may have the nucleotide sequence as set forth in SEQ ID No:1.

According to another aspect of the invention, there is provided a mouse transgenic fertilized egg comprising an expression construct comprising (a) a nucleotide sequence encoding Y114F mutant prohibitin and (b) a transcription-regulating sequence operatively linked to the nucleotide sequence.

As will be appreciated by one of skill in the art, such a fertilized egg comprising the expression construct may be generated using a variety of means known in the art. The fertilized egg may then be implanted into a suitable host for generation of a transgenic mouse as described above.

Preferably, the nucleotide sequence encoding prohibitin comprises the nucleotide sequence deduced from the amino acid sequence as set forth in SEQ ID No:3.

The transcription-regulating sequence may be aP2 promoter. Preferably, the aP2 promoter comprises the nucleotide sequence as set forth in SEQ ID No:1.

Preferably, the expression construct is integrated into the genome of the mouse transgenic fertilized egg.

According to another aspect of the invention, there is provided an isolated totipotent mouse cell comprising an exogenous nucleic acid construct that comprises Y114F mutant prohibitin operably linked to a suitable promoter.

Preferably, the exogenous nucleic acid construct encoding prohibitin comprises the nucleotide sequence deduced from the amino acid sequence as set forth in SEQ ID No:3.

Preferably, the suitable promoter comprises aP2 promoter.

Preferably, the aP2 promoter comprises the nucleotide sequence as set forth in SEQ ID No:1.

Preferably, the exogenous nucleic acid construct is integrated into the genome of the mouse cell.

It is of note that similar to the NASH and HCC model (Mito-Ob) discussed above, targeting insulin resistance (by improving insulin sensitivity and reducing hyperinsulinemia) and reducing low-grade inflammation by anti-inflammatory compound either alone and in different combination.

According to a still further aspect of the invention, there is provided a method of determining if a compound of interest reduces severity of histiocytosis comprising:

growing a transgenic mouse overexpressing the Y114F mutant prohibitin (PHB) to approximately at least 3 months of age;

administering the compound of interest to the transgenic mouse; and determining if the compound of interest delays onset or reduces severity of histiocytosis.

It is of note that this may be determined by comparison with an untreated or mock treated control. Furthermore, it is of note that the control does not necessarily need to be repeated for each compound.

That is, the compound of interest may delay the onset of histiocytosis past 6 months of age.

As will be appreciated by one of skill in the art, the compound may be administered according to a regimen. For example, the compound of interest may be administered daily for a period of time. Daily administration may be once per day or may be multiple times per day. Furthermore, "daily" administration may also refer to for example administration every other day, two out of three days, 5 out of 7 or any other similar dosage regimen known to and used by those of skill in the art.

As will be appreciated by one of skill in the art, administration of the compound does not necessarily need to begin at 3 months. For example, administration may begin shortly before onset of histoiocytosis, at onset of histiocytosis or shortly after onset of histiocytosis. In this manner, compounds can be tested for efficacy at treating lymphadenopathy at different stages of the disease.

As discussed above, the compound may be a compound known to have or suspected of having anti-inflammation properties and/or be a compound known or suspected to target insulin resistance. Alternatively, the compound may be a compound not specifically known or suspected of having these properties and/or may be a compound that has no known or suspected properties. In preferred embodiments, the compound of interest is administered at an amount or concentration such that the known or suspected or theoretical properties are expected or anticipated to be observed.

According to an aspect of the invention, there is provided a method of determining if a compound of interest reduces severity of lymphadenopathy comprising:

growing a transgenic mouse overexpressing the Y114F mutant prohibitin (PHB) to approximately at least 3 months of age;

administering the compound of interest to the transgenic mouse; and determining if the compound of interest delays onset or reduces severity of lymphadenopathy. Specifically, the compound may reduce the severity of one or more symptoms associated with lymphadenopathy, for example, reduction in swelling of lymph nodes compared to a control.

It is of note that this may be determined by comparison with an untreated or mock treated control. Furthermore, it is of note that the control does not necessarily need to be repeated for each compound.

That is, the compound of interest may delay the onset of lymphadenopathy past 6 months of age. Alternatively, the compound may or may also delay the onset lymph node tumors past 9 months of age.

As will be appreciated by one of skill in the art, the compound may be administered according to a regimen.

As will be appreciated by one of skill in the art, administration of the compound does not necessarily need to begin at 3 months. For example, administration may begin shortly before onset of lymphadenopathy, at onset of lymphadenopathy, shortly after onset of lymphadenopathy, shortly before onset of lymph node tumors or at onset of lymph node tumors. In this manner, compounds can be tested for efficacy at treating lymphadenopathy at different stages of the disease.

As discussed above, the compound may be a compound known to have or suspected of having anti-inflammation properties and/or be a compound known or suspected to target insulin resistance. Alternatively, the compound may be a compound not specifically known or suspected of having these properties and/or may be a compound that has no known or suspected properties.

The invention will now be further elucidated by way of examples; however, the invention is not necessarily limited to the examples.

Mito-Ob Mice Display Sex Differences in Adipose Tissue Structure and Function, and in Metabolic Dysregulation Visceral adipose tissue inflammation plays a critical role in obesity associated systemic metabolic dysregulation in both humans and mice (Huh et al., 2014, Mol Cells 37: 365-371). The sexually dimorphic metabolic phenotype of Mito-Ob mice prompted us to investigate the inflammatory status of their adipose tissues. Immunohistochemical analysis using macrophage specific marker antibody CD68 revealed a significant increase in the inflammatory macrophages in male Mito-Ob mice compared to wild-type mice (FIG. 1A). This difference was not observed between female Mito-Ob mice and control mice, despite comparable obesity and adipocyte hypertrophy in both male and female Mito-Ob mice (FIG. 1B). Consistent with the histological phenotype of adipose tissue, a sex-dimorphic change in adiponectin and leptin was also found. Adiponectin level was significantly upregulated in female Mito-Ob mice and down regulated in male Mito-Ob mice in comparison with respective control mice (FIG. 1B), whereas an inverse trend was found in the leptin level. Resistin level did not show significant differences in male and female Mito-Ob mice compared with respective control mice. Fasting serum insulin level was significantly upregulated in male Mito-Ob mice compared with control mice, whereas female Mito-Ob mice had insulin level similar to wild type mice (FIG. 1C). Unexpectedly and surprisingly, Mito-Ob mice showed inverse alteration in anti-inflammatory peptide ghrelin levels between male and female mice. The serum ghrelin level was significantly increased in the female mice compared with wild type control mice. In contrast, male Mito-Ob had significantly reduced ghrelin level compared with wild type control mice (FIG. 1C). This would imply that ghrelin might have a role in sexually dimorphic metabolic phenotype in male Mito-Ob mice. Taken together, these data indicate that Mito-Ob mice exhibit sex differences in visceral adipose tissue structure and function, and inverse alteration in serum ghrelin levels that correlate with sexually dimorphic metabolic phenotype of Mito-Ob mice.

Hepatic Steatosis in Male Mito-Ob Progresses to Steatohepatitis with Aging

Figure 2:
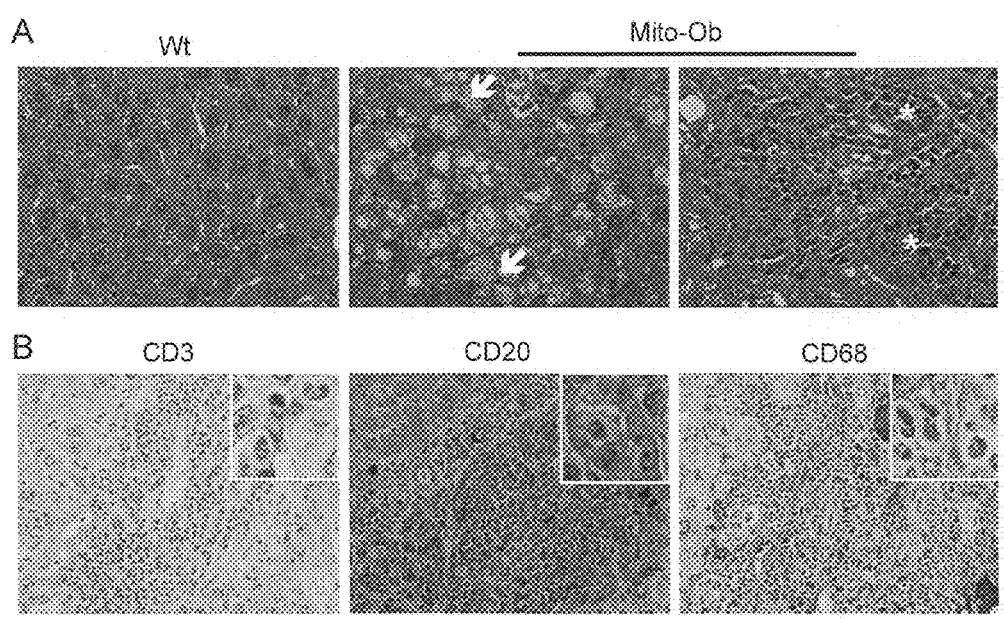
FIG. 2. Hepatic steatosis in male Mito-Ob progresses to steatohepatitis with aging. (A) Representative photomicrographs showing histological structure of the liver of Mito-Ob mice and their age matched wild type littermates at 9 months of age. Hepatocyte ballooning and immune infiltration, a sign of steatohepatitis, are indicated with white arrow and asterisk respectively. Scale bars, 20 µm. (B) Representative photomicrographs showing inflammation and immune infiltration status in the liver from Mita-Ob mice as determined by immunohisto-chemistry using macrophage and lymphocyte specific marker antibodies. Scale bars, 20 µm. (n=4-6 mice in each group).

Sex specific hyperinsulinemia and ectopic fat accumulation in the liver in male Mito-Ob at 6 months of age, as found in our previous study; lead us to investigate the hepatic phenotype with aging. Histological examination of the liver at 9 months of age showed signs of NAFLD progression to NASH in male Mito-Ob mice as revealed by the characteristic ballooning of hepatocytes and lymphocyte infiltration (FIG. 2A), both of which are important diagnostic features of human NASH (Brunt et al., 2001, Semin Liver Dis 21: 3-16). Increased inflammatory macrophages and immune infiltration in the liver was further confirmed by immunohistochemical analysis using macrophage and lymphocyte specific marker antibody (FIG. 2B). Lymphocytes were predominantly positive for CD20 and CD68, and only few were CD3 positive (FIG. 2B). Taken together, these data indicate that obesity associated NAFLD in the male Mito-Ob spontaneously progress to NASH with aging.

The Male Mito-Ob Mice Spontaneously Develop HCC with Aging

Figure 3:
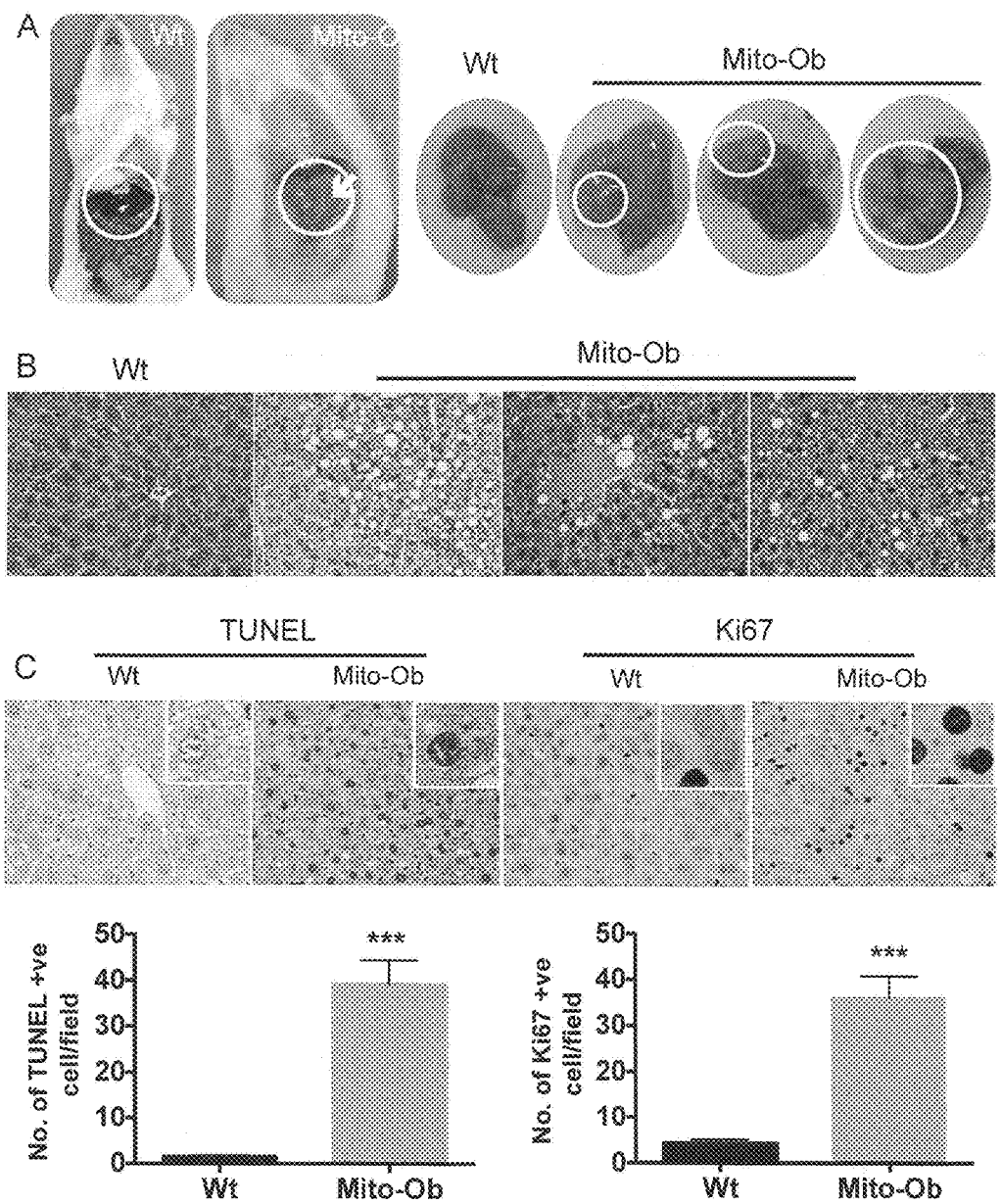
FIG. 3. The male Mito-Ob mice spontaneously develop HCC with aging. (A) Representative photographs showing liver morphology in situ from 12-14 months old Mito-Ob mice and their wild type littermates. Tumor development in the male Mito-Ob mice is indicated with white arrow. Representative photomicrographs showing histological architecture of H & E stained liver tumor (B), apoptotic cells death as determined by TUNEL assay (C) and cell proliferation as determined by anti-Ki67 antibody (D). (E) Histograms showing quantification of cell death and cell proliferation in the liver as determined in panel C and D. Magnified view of the nucleus is shown in the inset. Data are presented as mean±SEM (n=5-7 mice in each group). Asterisks indicate comparison between sex matched Mito-Ob vs Wt. NS, not significant; ***P<0.001 by Student's t test. Wt—wild type.

Interestingly, in our follow-up study we found that the male Mito-Ob mice start to develop pale to whitish nodular tumors (2-4 mm) on liver surface around 10-12 months of age, which progressively grew into multifocal larger tumors (6-8 mm) by 12-14 months of age (FIG. 3A), with a prevalence of ~20%. Histological analysis confirmed tissue structure characteristic of HCC (FIG. 3B). Tissue necrosis and anisocytosis of hepatic nuclei were also apparent (FIG. 3B). Apoptotic cell death as determined by TUNEL staining were significantly increased in the liver of male Mito-Ob mice compared with control mice (FIG. 3C). A parallel increase in Ki67-positive proliferating cells was also observed in the liver of male Mito-Ob mice (FIG. 3C). Thus, male Mito-Ob mice showed continuous hepatocyte death and compensatory proliferation, a critical process in hepatocarcinogenesis (Nakagawa et al., 2014; Maeda et al., 2005, Hepatogastroenterology 52: 187-190).

Male Mito-Ob Mice with NASH/HCC Exhibit Mitochondrial Dysregulation

Figure 4:
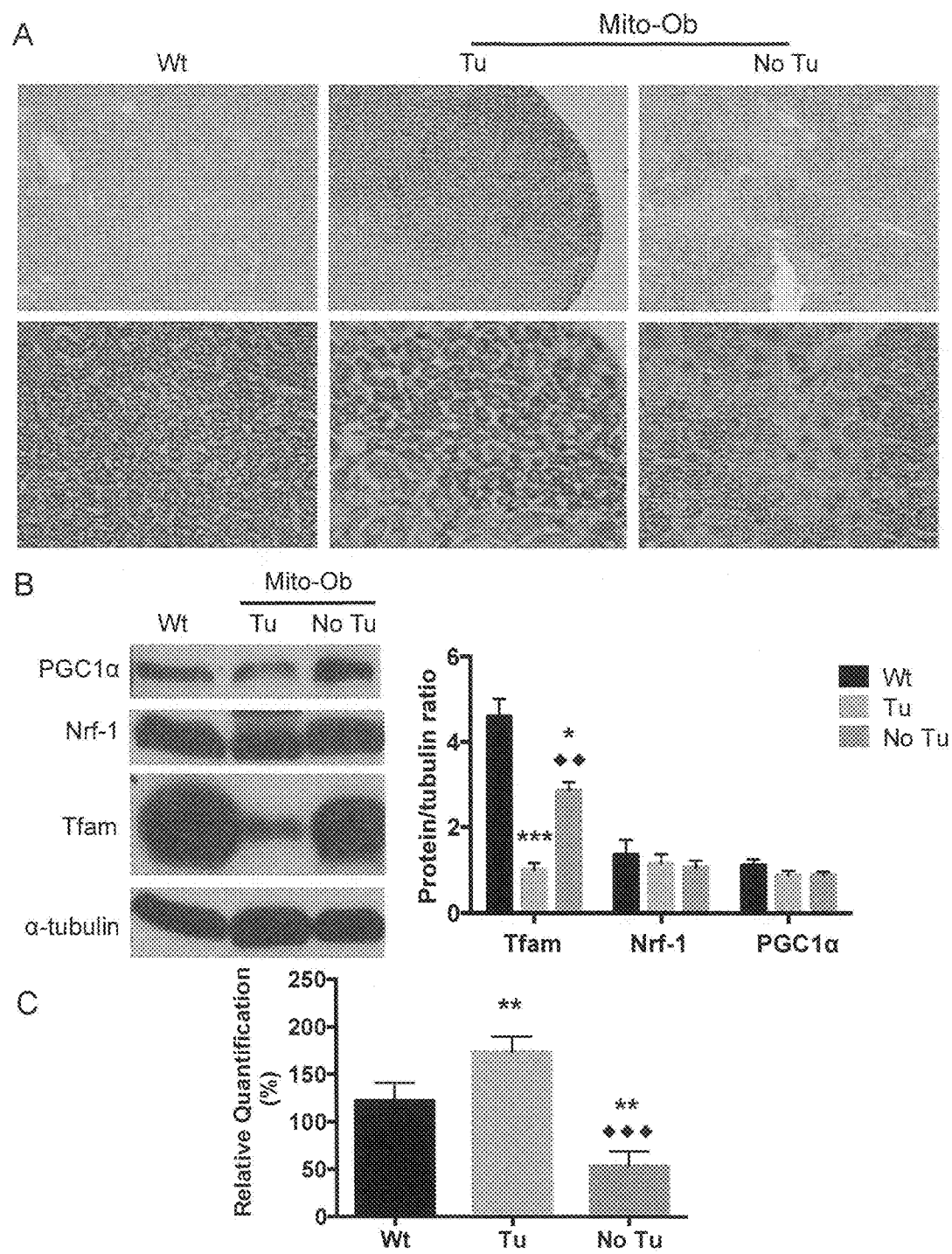
FIG. 4. Male Mito-Ob mice with HCC exhibit mitochondrial dysregulation. (A) Representative photomicrographs showing reduction in mitochondria content in the hepatic lesion as determined by immunohistochemistry using anti-prohibitin antibody. (B) Left panel: Representative immunoblots showing expression level of mitochondrial marker proteins in the liver from Mito-Ob mice control mice. Nrf-1 was used as a control for nuclear transcription factor and beta-tubulin blot is shown as a loading control. Right panel: Histograms showing quantification of protein levels. Data are presented as mean±SEM (n=5-7 mice in each group). Asterisks indicate comparison between sex matched Mito-Ob vs Wt. NS, not significant; *P<0.05, P<0.01, *P<0.001 by Student's t test. Diamonds indicate comparison between Tu and No Tu group by Student's t test. Wt—wild type; Tu—tumor; No Tu—No tumor.

Glucose and lipid toxicity as well as chronic low-grade inflammation are known to cause mitochondrial dysregulation (Rossignol et al., 2014), and emerging evidence suggests that mitochondrial dysregulation in hepatocytes precedes the onset of HCC (Koliaki et al., 2015, Cell Metab 21: 739-746). Because the male Mito-Ob mice display all these causative signs, therefore, we sought to know the mitochondrial status in tumor bearing liver. Immunohistochemical analysis using mitochondrial marker specific antibody showed a differential staining pattern in the liver tissue with hepatic lesions, which was significantly diminished in the hepatic lesions compared with area having normal histological architecture (FIG. 4), suggesting a relationship between hepatic lesion and mitochondrial dysregulation. Liver from wild-type mice showed a homogenous staining pattern (FIG. 4). Mitochondrial transcription factor A (Tfam) and COX-IV levels were significantly decreased in the liver from male Mito-Ob compared with wild type mice as determined by western immunoblotting, which was further reduced in the liver from tumor bearing mice (FIG. 4B). This difference was not observed in the expression level of nuclear transcription factor-1 (Nrf-1) required for nuclear encoded mitochondrial proteins (FIG. 4B). The expression level of PPARγ-coactivator-1α (PGC-1α), showed a trend similar to Tfam protein level, however, it was not statistically different between different groups. Taken together, these data indicate that hepatic phenotype in the male Mito-Ob mice mimics obesity associated mitochondrial dysregulation in steatohepatitis and HCC in humans.

Male Mito-Ob Mice with HCC Show Increased Hepatic Oxidative DNA Damage

Figure 5:
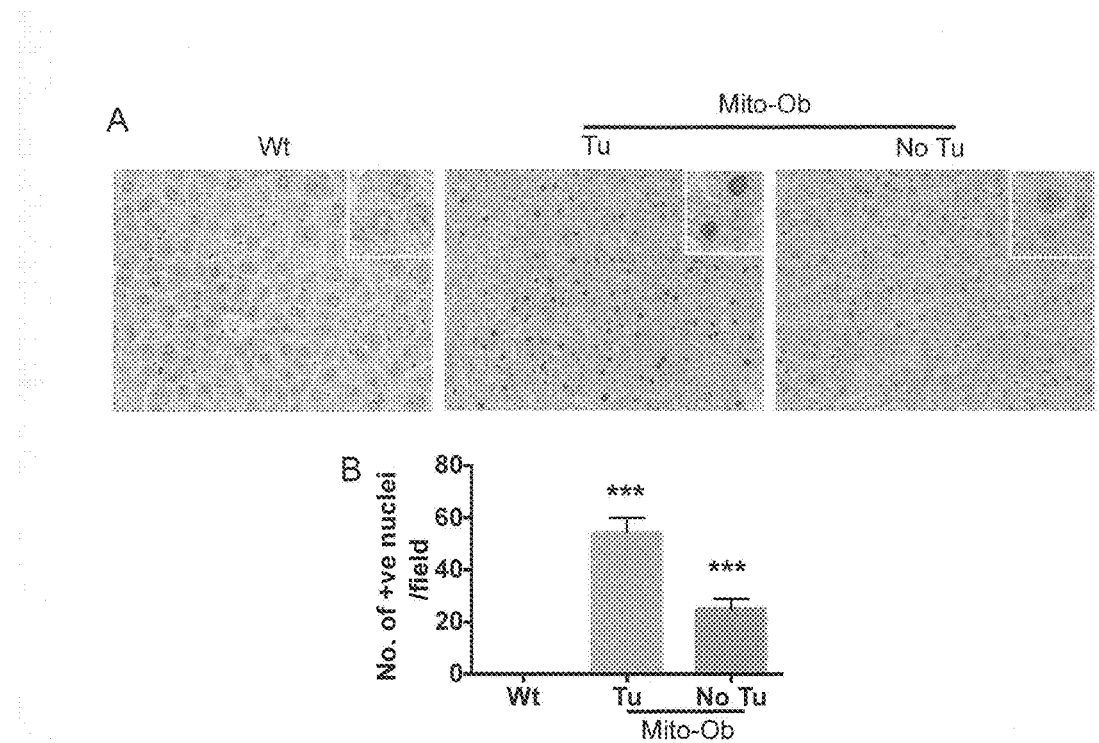
FIG. 5. Male Mito-Ob mice with HCC show increased hepatic oxidative DNA damage. Representative photomicrographs showing oxidative DNA damage in the liver at 12-14 months of age. Histograms showing quantification of oxidative DNA damage in the liver as shown in the upper panel. Data are presented as mean±SEM (n=5-7 mice in each group). Asterisks indicate comparison between sex matched Mito-Ob vs Wt. NS, not significant; *P<0.05, P<0.01, *P<0.001 by Student's t test.

To further explore the link between mitochondrial dysregulation and HCC development in male Mito-Ob mice, we measured oxidative DNA damage using ROS antibody (Biorbyt Ltd, UK). Hepatic oxidative DNA damage was significantly increased in the liver of Mito-Ob/Tu compared with Mito-Ob mice without tumor and wild type mice (FIG. 5). No difference in oxidative DNA damage was found between in wild type and Mito-Ob mice without tumor (FIG. 5). Collectively, these data point towards a role of oxidative stress in obesity-linked pathogenesis of HCC.

Figure 6:
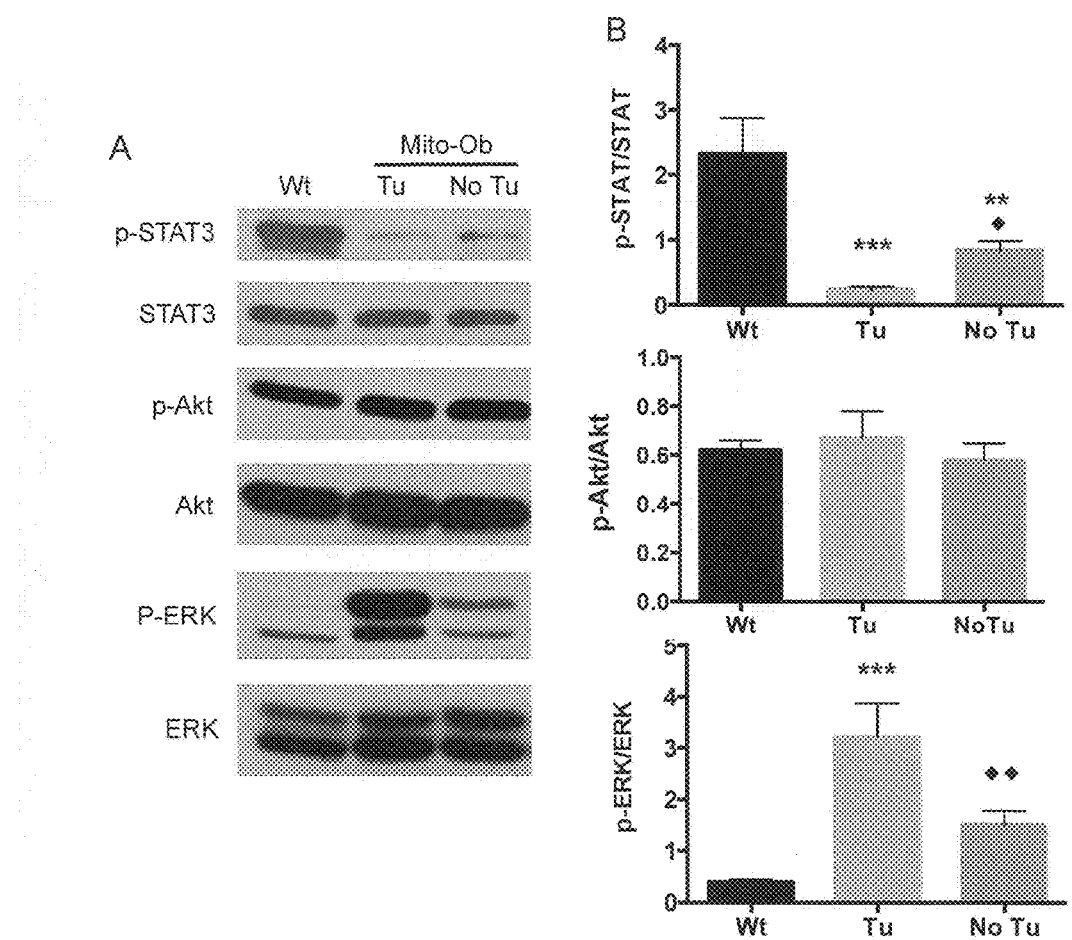
FIG. 6. ERK1/2 and STAT3 signaling are inversely altered in the liver tumors from Mito-Ob mice. (A) Representative immunoblots showing the activation level of Akt, ERK, and STAT3 signaling pathways in the liver at 12-14 months of age as determined by their phospho-specific antibodies. (B) Histograms showing quantification of the activation level of Akt, ERK, and STAT3 in the liver as shown in the upper panel. Data are presented as mean±SEM (n=5-7 mice in each group). Asterisks indicate comparison between sex matched Mito-Ob vs Wt. NS, not significant; *P<0.05, P<0.01, *P<0.001 by Student's t test. Diamonds indicate comparison between Tu and No Tu group by Student's t test. Wt—wild type; Tu—tumor; No Tu—No tumor.
Figure 7:
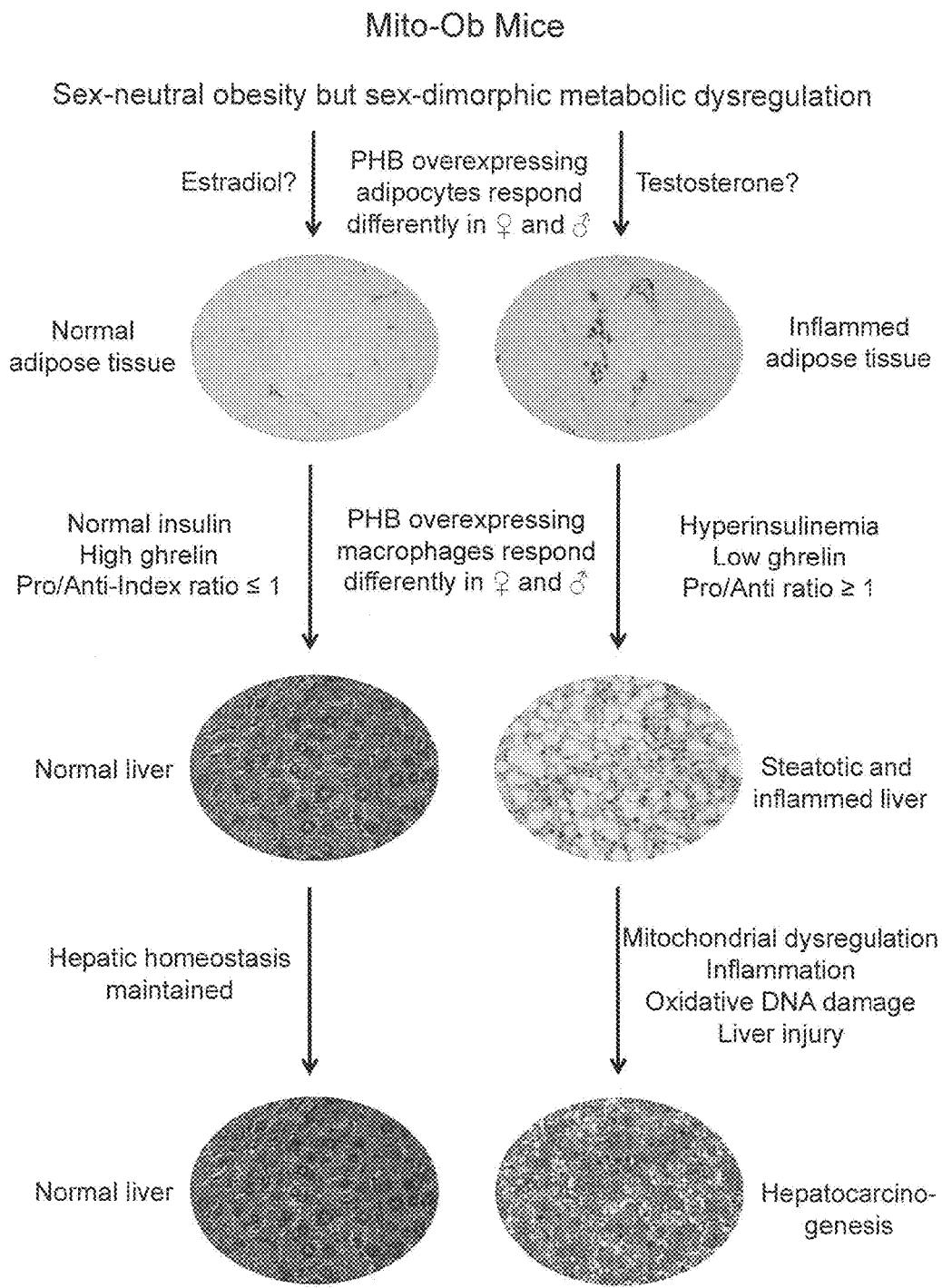
FIG. 7. Schematic diagram showing proposed mechanism in obesity-linked NASH and HCC development.

ERK1/2 and STAT3 Signaling are Inversely Altered in the Liver Tumors from Mito-Ob Mice To get insight into the cell signaling pathway involved in HCC development in Mito-Ob mice, we determined the activation level of PI3K/Akt, MAPK/ERK and STAT3 signaling pathways because they have been implicated in the pathogenesis of HCC (Nakagawa et al., 2014; Umemura et al., 2014; Duan et al., 2014), and have been shown to be modulated by PHB in other cell/tissue type (Mishra et al., 2010, FEBS J 277: 3937-3946). Phopsho-ERK (p-ERK1/2) level was significantly increased in the liver from male Mito-Ob mice compared with wild type mice, which is further increased in tumor bearing liver (FIG. 6). In contrast, p-STAT3 level showed an inverse relationship with p-ERK activation level (FIG. 6). No significant change in p-Akt level was found in the liver from Mito-Ob/Tu and Mito-Ob mice in comparison with wild type mice (FIG. 6). Taken together, these data indicate a role of increased oncogenic mediator p-ERK and decreased pSTAT3 in the liver tumor development in male Mito-Ob mice.

The m-Mito-Ob Mice Share the Metabolic Phenotype of Mito-Ob Mice

Figure 8:
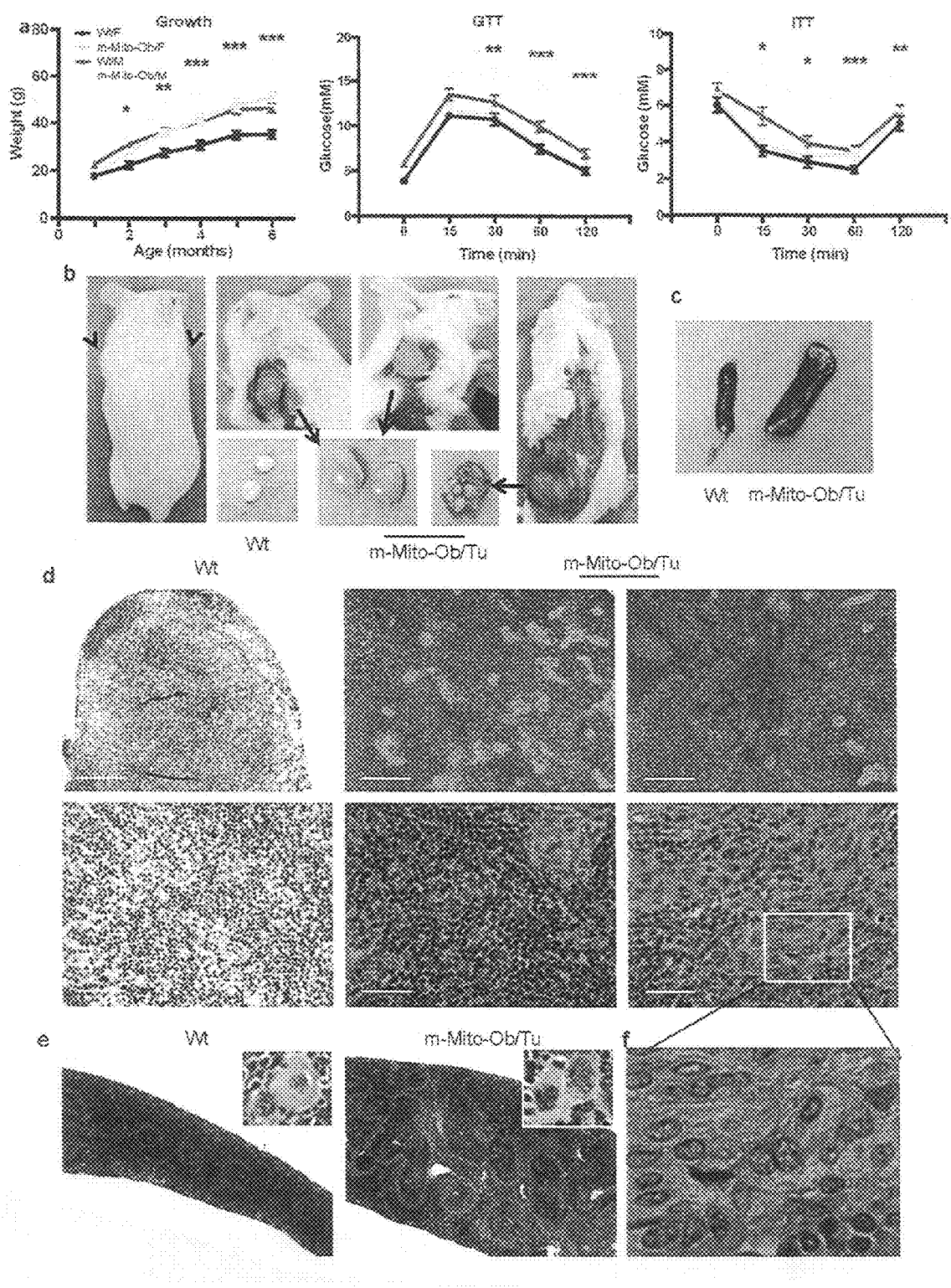
FIG. 8. The m-Mito-Ob mice share the metabolic phenotype of Mito-Ob mice but develop tumors. (a) Line graphs showing growth curve, glucose tolerance test (GTT), insulin tolerance test (ITT) in m-Mito-Ob mice and their wild-type littermates at 6 months of age. Data are presented as mean±SEM (n=6-9 animals in each group). *p<0.05; p<0.01; *p<0.001 by Student t test between sex-matched m-Mito-Ob and Wt mice. (b) Representative photographs showing tumor development in axillary and inguinal lymph nodes (black arrowhead or arrow). (c) Representative photographs of the spleen from male wild type and m-Mito-Ob/Tu mice. (d) Representative photomicrographs showing H & E stained tumors from m-Mito-Ob/Tu mice and lymph node from wild type mice for reference (Scale bars=50 µm and 20 µm for upper and lower panel respectively). Magnified view of histiocytes within boxed area is shown in panel (f) to better visualize the nuclear structure. (e) Representative photomicrographs of H & E stained spleen from male m-Mito-Ob/Tu and wild type mice (Scale bars=50 µm). Magnified views of Reed-Steinberg cells are shown in the inset in each case.

To determine whether substitution of tyrosine-114 by phenylalanine (Y114F) in PHB protein affects its adipogenic function and the metabolic phenotype of Mito-Ob (Ande et al., 2014), we measured growth, glucose homeostasis and insulin sensitivity in m-Mito-Ob mice. Similar to Mito-Ob mice (Ande et al., 2014), the m-Mito-Ob mice started to gain weight around one month of age and became significantly obese ($p<0.05$-$0.001$) by 2-3 months of age compared with wild-type littermates (FIG. 8a), independent of diet. Glucose and insulin tolerance tests revealed that similar to male Mito-Ob mice (Ande et al., 2014), the male m-Mito-Ob mice had impaired glucose and insulin tolerance compared with their wild-type littermates ($p<0.05$-$0.001$) at six months of age (FIG. 8a). Likewise, female m-Mito-Ob mice were found to have glucose tolerance and insulin sensitivity similar to wild-type mice (FIG. 8) (Ande et al., 2014). Collectively, these data indicate that mutating tyrosine-114 phosphorylation site in PHB does not affect its adipogenic/ glucoregulatory function and m-Mito-Ob mice share the metabolic phenotype of age and sex matched Mito-Ob mice.

The Male m-Mito-Ob Mice Develop Sinus Histiocytosis with Lymphadenopathy

Figure 9:
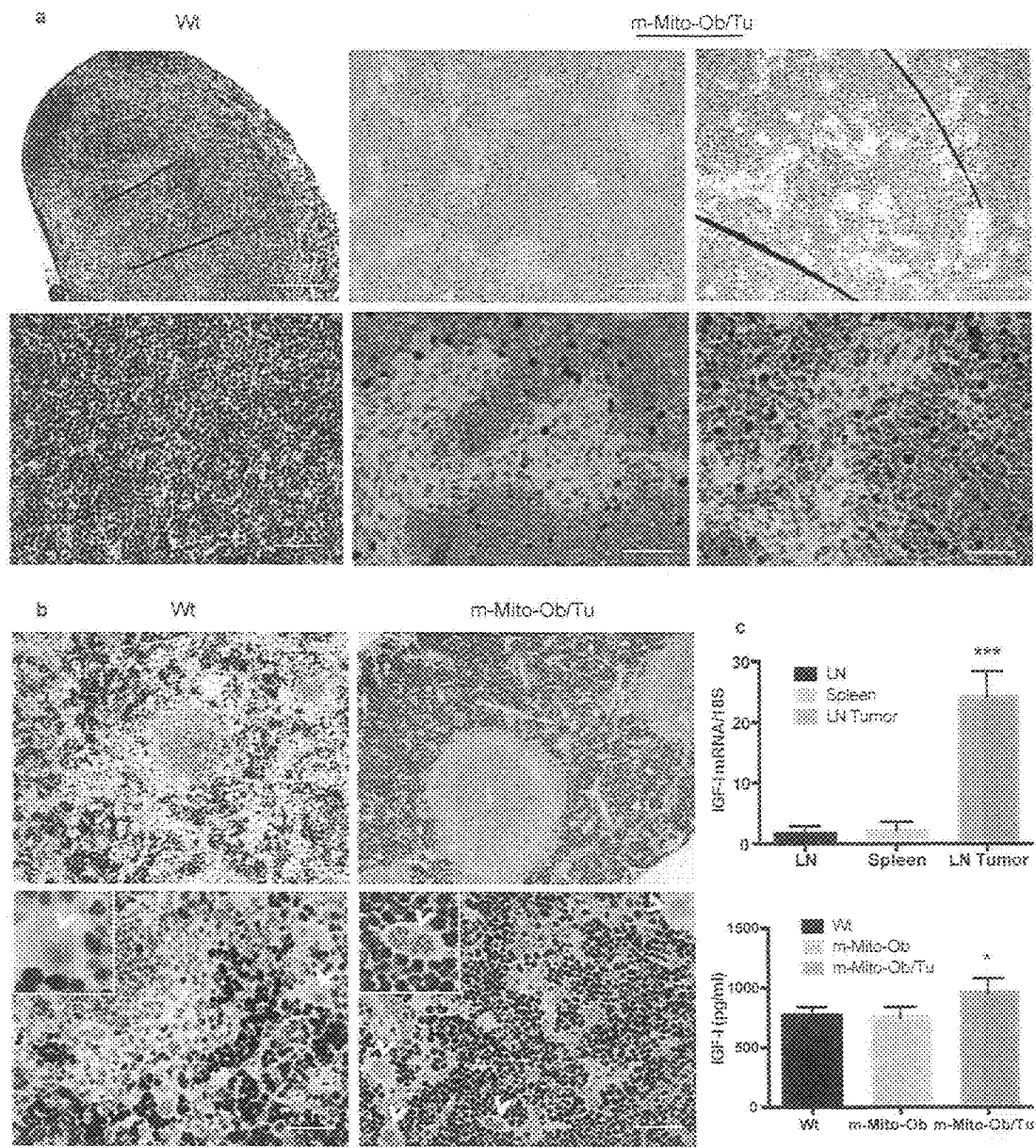
FIG. 9. Histiocytes in the tumors are proliferative. Representative photomicrographs showing immunohistochemical analysis of Ki-67 positive cells in the tumors (panel a) and the spleen (panel b) from m-Mito-Ob/Tu mice. Magnified views of Reed-Steinberg cells (white arrow head) are shown in the inset in each case. Scale bars=50 µm and 20 µm for upper and lower panel respectively. (c) Histograms showing IGF-I mRNA expression in the tumors and serum IGF-I levels from m-Mito-Ob mice as determined by real-time PCR and ELISA respectively. Data are presented as mean±SEM (n=3-5 animals in each group). *p<0.05; ***p<0.001 by Dunnett's t test between sex-matched wild type and m-Mito-Ob or m-Mito-Ob/Tu mice.

Interestingly, the male m-Mito-Ob mice started to develop multiple palpable tumors around 9 months of age (FIG. 8b), with a prevalence of ~50%. In general, the tumors developed unilaterally or bilaterally in the axillary and/or inguinal lymph nodes, near the fore limbs and hind limbs respectively (FIG. 8b). Histological analysis revealed tissue structure characteristic of sinus histiocytosis with lymphadenopathy, and showed gradual expansion of eosinophilic histiocytes within lymph nodes during tumor growth (FIG. 8d). Histiocytes were much larger with indented or grooved nuclei and voluminous pale and eosinophilic cytoplasm that sometimes showed fine vacuoles (FIG. 8d). In addition, histiocytes were elongated with less distinct cell borders and were proliferative in their appearance (FIG. 8d,f), which was confirmed by immunohistochemical staining using anti-Ki-67 antibody (FIG. 9a). During the early stages of tumor development, the Ki-67 positive cells were patchy in their distribution, whereas at the later stages Ki-67 positive cells had homogenous and widespread distribution (FIG. 9a). In addition to histiocytes, an increase in lymphocyte population was apparent in tumors from m-Mito-Ob mice. The tumor bearing male m-Mito-Ob (m-Mito-Ob/Tu) mice also developed splenomegaly (FIG. 8c). Upon histological analysis, the spleen was found to contain larger follicles, expanded cortical area and increased population of Reed-Steinberg cells (also known as lacunar histiocytes) in comparison with spleen from wild-type mice (FIG. 8e). The spleen from m-Mito-Ob/Tu mice was almost packed with Ki-67 positive lymphocytes except in follicles where Ki-67 positive cells showed scattered distribution (FIG. 9b). The Reid-Steinberg cells were also found positive for Ki-67 in the spleen of m-Mito-Ob/Tu mice (FIG. 9b). The Reed-Steinberg cells were not observed in the tumors. IGF-I mRNA expression was found significantly upregulated ($p<0.001$) in the tumors but not in the spleen from m-Mito-Ob/Tu mice compared to lymph nodes from wild-type mice (FIG. 9c). Serum IGF-1 level was significantly increased in m-Mita-Ob/Tu mice ($p<0.05$) compared to wild type and m-Mito-Ob mice that did not develop tumor (FIG. 9c).

The m-Mito-013/Tu Mice Develop Heterogeneous Histiocytosis

Figure 10:
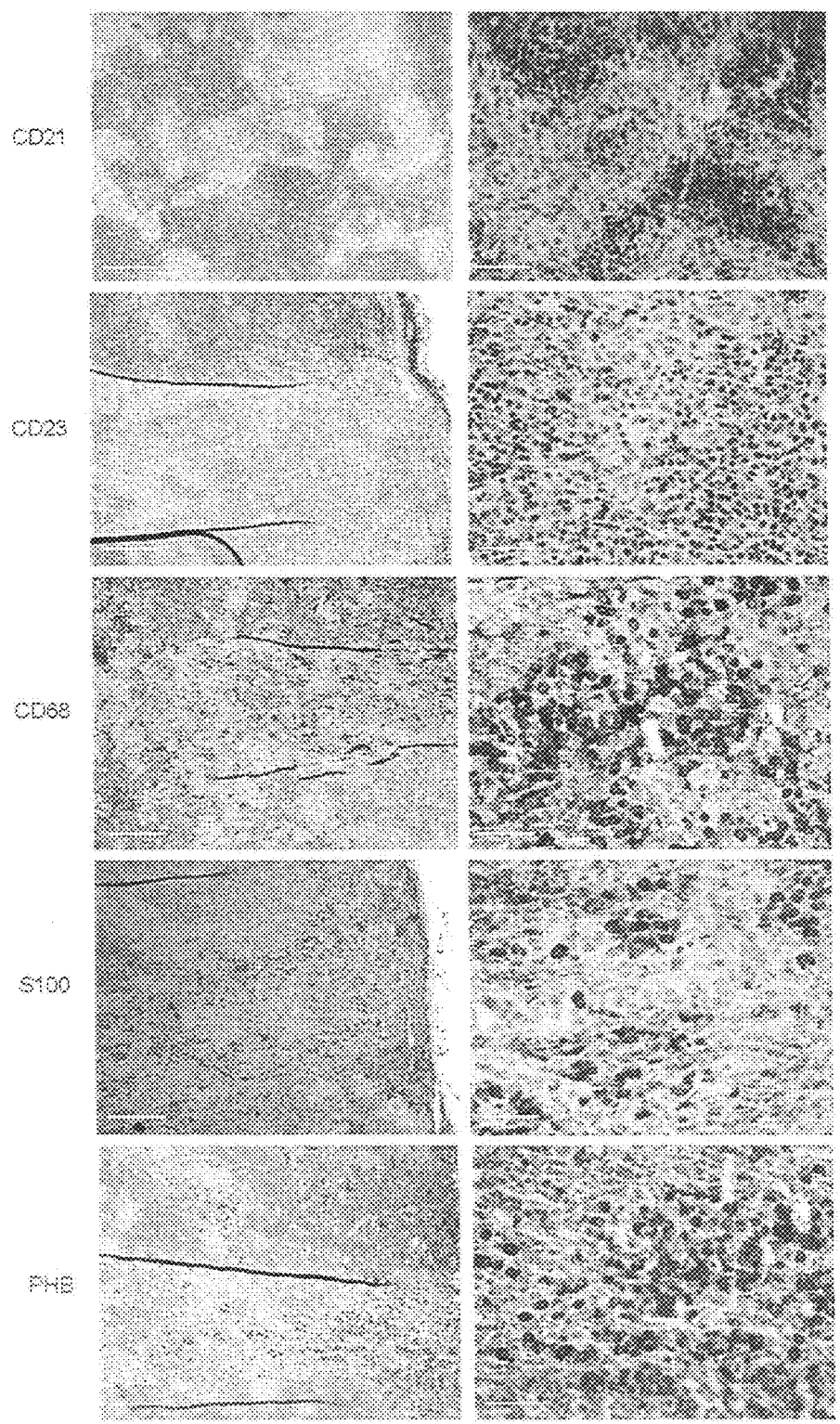
FIG. 10. Histiocytoses in male m-Mito-Ob/Tu mice are heterogeneous in nature. Representative photomicrographs showing immunohistochemical characterization of histiocytes in the tumors from male m-Mito-Ob/Tu mice using cell type specific marker antibodies. Scale bars=50 µm and 20 µm for the left and the right panel respectively.

To further characterize the histiocytic and dendritic cell subtypes in the tumors from m-Mito-Ob/Tu mice, we performed immunohistochemical analyses using their marker antibodies (Roding et al., 2013). The tumors were found positive for CD68 staining suggesting their histiocytic origin (FIG. 10). As expected, histiocytes were positive for PHB and showed staining pattern similar to CD68 staining (FIG. 10). The tumors were also found positive for S100, a marker for dendritic cells (FIG. 10). However, the staining pattern of S100 was often patchy rather than widespread like CD68 staining (FIG. 10). The tumors were negative for CD21 and CD23 antibodies suggesting the presence of dendritic cells other than follicular dendritic cells (FIG. 10) (Roding et al., 2013). CD68 and S100 staining pattern were predominantly cell membrane and cytoplasmic (FIG. 10). Collectively, these results suggest that m-Mito-Ob/Tu mice develop heterogeneous histiocytosis containing histiocytic and dendritic cells.

Tumor Development in m-Mito-Ob Requires Both Hyperinsulinemia and m-PHB

A careful and systematic analysis of the metabolic status and tumor development in m-Mito-Ob revealed that histiocytosis developed only in insulin resistant male m-Mito-Ob mice (~50%, 12 out of 23 mice). The female m-Mito-Ob mice, despite having visceral obesity similar to male m-Mito-Ob mice had normal glucose and insulin tolerance (FIG. 8a), and did not develop tumor suggesting m-PHB in itself is not sufficient for the development of histiocytosis and may serve as a dormant clone. Furthermore, the male Mita-Ob mice that developed obesity and obesity associated insulin resistance (Ande et al., 2014) similar to m-Mito-Ob (FIG. 8a) but lacking m-PHB, did not develop tumor. Taken together, these data suggest that the development of histiocytosis with lymphadenopathy in m-Mito-Ob mice requires both obesity-associated hyperinsulinemia and m-PHB.

Serum Hormone and Adipokine Profiles

Serum insulin levels were significantly higher ($p<0.01$) in male m-Mito-Ob mice compared with wild-type mice under both fasting and fed conditions (Table 1). However, female m-Mito-Ob mice had insulin levels similar to control female mice (Table 1). Interestingly, a sex-dimorphic change in serum ghrelin levels was found in m-Mito-Ob mice in comparison with age and sex matched wild-type mice (Table 1). The serum ghrelin level in female m-Mito-Ob mice was significantly increased under fasting condition in comparison with wild-type female mice ($p<0.001$) whereas in male m-Mito-Ob mice the serum ghrelin level was significantly decreased in both fasting and fed conditions ($p<0.001$) in comparison with wild-type male mice (Table 1). No significant difference in the serum ghrelin level was found between wild-type male and female mice under fasting and fed conditions (Table 1). Taken together, these data would suggest that an inverse and sex-dimorphic change in serum insulin and ghrelin levels in m-Mito-Ob mice is due to m-PHB overexpression, and may have a role in sex-dimorphic phenotype in m-Mito-Ob mice. Among adipokines, adiponectin levels were increased ($p<0.05$) only in female m-Mito-Ob mice compared with control mice (Table 1), whereas leptin levels were higher in male m-Mito-Ob mice than in females (Table 1). Resistin levels were similar in the male m-Mito-Ob mice compared with control mice (Table 1).

Serum Cytokine Profiles

PHB was initially identified in association with IgM receptor (Terashima et al., 1994, EMBO J 13: 3782-3792). Recently, it has been shown to have a role in immune signaling and reported to be a host target protein by a number of pathogens (Sharma et al., 2004; Richter et al., 2014). Because a compromised immune defense is a common feature of the pathogenesis of various diseases including tumor development (Rutkowski et al., 2015, Cancer Cell 27: 27-40), we measured serum cytokine levels to assess the potential contribution of whole body immune status in tumor development in m-Mito-Ob mice. IL-2, IL-6, IL10, IL-12 INF-γ and TNF-α levels were significantly decreased in m-Mito-Ob/Tu mice (and to a lesser extent in non-tumor bearing m-Mito-Ob mice) in comparison with wild-type mice (Table 2). Female m-Mito-Ob mice had higher cytokines levels especially anti-inflammatory cytokines in comparison with female wild-type mice (Table 2). Collectively, this data indicates that male m-Mito-Ob/Tu mice had significantly attenuated immune response or antitumor immunity, whereas female m-Mito-Ob mice had augmented immune response. Together, these data indicate a role of reduced immune response in the tumor development in male m-Mito-Ob mice.

Serum Chemokine Profiles

Figure 11:
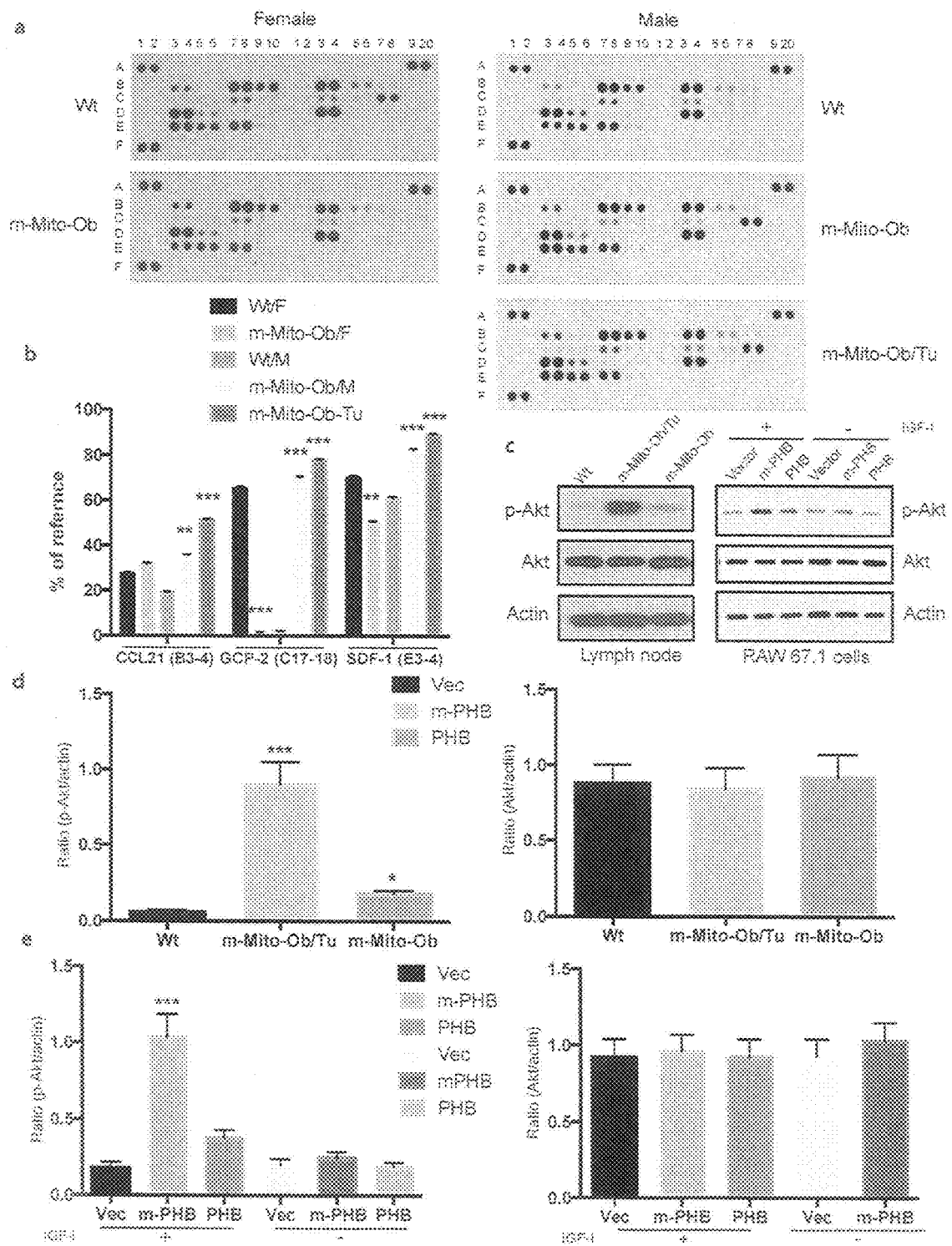
FIG. 11. Serum chemokines profiles and Akt activation status in the tumors of m-Mito-Ob mice. (a) Representative chemokine protein array blots showing serum chemokines in wild type and m-Mito-Ob mice. A1-2, A19-20 and F1-2 in each array blot represents reference spots. (b) Histograms showing quantification of significantly altered chemokines in m-Mito-Ob/m-Mito-Ob/Tu mice from wild type mice. Data are presented as mean±SEM (n=3 animals in each group). Spot ID on the X-axis are shown in parentheses. p<0.01; *p<0.001 by Student t test or Dunnett's t test (c) Representative immunoblots showing activation levels of Akt in the tumor samples and RAW264.7 cells transfected with various PHB constructs. Lymph nodes from sex matched wild type mice and only vector-transfected cells were included as controls. (d) Histograms showing quantification of Akt activation status in tumor samples as shown in panel (c). (e) Histograms showing quantification of Akt activation status in RAW264.7 cells as shown in panel (c). Data are presented as mean±SEM (n=3 animals in each group; cell culture experiments were repeated three times). *p<0.05; ***p<0.001 by Student t test or Dunnett's t test.

Chemokines released from adipocytes are known to play a critical role in the recruitment of immune cells including macrophages to the adipose tissue and in the phenotypic switch from anti-inflammatory to pro-inflammatory type (Schipper et al., 2012, Trends Endocrinol Metab 23: 407-415; Venkan et al., 2013, J Hepatol SO168-8278: 00597). To explore the potential involvement of chemokines in sex dimorphic metabolic phenotype of m-Mito-Ob mice, we measured serum chemokine levels using chemokine protein array. Out of 28 chemokines analyzed, two of them (SDF-1, also known as CXCL12 and GCP-2, also known as ENA-78) in particular showed sex-dimorphic changes in m-Mito-Ob mice in comparison with their wild-type littermates (FIG. 11a,b). Both were significantly decreased in female m-Mito-Ob mice ($p<0.01$-$0.001$), whereas their levels were significantly increased ($p<0.001$) in male m-Mito-Ob and m-Mito-Ob/Tu mice (FIG. 11a,b). Notably, GCP-2 level showed dramatic and opposite change in female and male m-Mito-Ob mice respective to their control mice. GCP-2 was almost undetectable in female m-Mito-Ob mice whereas it was significantly upregulated in m-Mito-Ob mice (FIG. 11a,b; $p<0.001$). In addition, CCL21 (also known as 6Ckine) level was significantly increased in male m-Mito-Ob mice compared with control male mice ($p<0.01$), which was further increased in m-Mito-Ob/Tu mice ($p<0.001$; FIG. 11a,b). Taken together, these data suggest a role of SDF-1, GCP-2 and CCL21 in sex-dimorphic phenotype in m-Mito-Ob mice and potentially in facilitating tumor development in m-Mito-Ob/Tu mice.

Phospho-Akt (p-Akt) is Upregulated in the Tumors of m-Mito-Ob Mice

Previously we have reported that PHB modulates PI3K/Akt signaling in a phosphorylation dependent manner (Ande et al., 2009; Ande et al., 2009, Biochem Biophys Res Commun 390: 1023-1028). PHB has also been reported to modulate MAPK/ERK signaling (Rajalingam et al., 2005). To determine which one of these two signaling arms is activated during the tumor development in m-Mito-Ob mice; we measured activation levels of Akt and ERK1/2 in tumors samples from m-Mito-Ob mice (Ande et al., 2012). Phospho-Akt (p-Akt) was found upregulated in the tumors from m-Mito-Ob/Tu mice compared with control lymph nodes from wild type and m-Mito-Ob mice (FIG. 11c,d). In contrast to p-Akt, p-ERK1/2 levels remain unchanged in the tumor samples in comparison with control lymph nodes. Collectively, this data suggests that Akt signaling pathway is selectively upregulated in tumors from m-Mito-Ob/Tu mice and may be a driving factor for increased proliferation of histiocytes.

To further confirm the role of m-PHB in the upregulation of Akt activation in macrophage specific manner, we studied the effect of m-PHB overexpression on Akt phosphorylation in response to IGF-I stimulation in RAW264.7 cells, a model murine macrophage cell line. A similar upregulation of Akt phosphorylation in RAW264.7 cells transfected with m-PHB was observed compared with vector or PHB transfected cells confirming that overexpression of m-PHB in macrophages upregulate Akt activation (FIG. 11c,e).

Materials and Methods
Transgenic Mice

The animals were given normal chow (LabDiet, St. Louis, Mo.) and water ad libitum. Body weight and food intake of Mito-Ob and wild-type mice was recorded on a regular basis.

The generation and characterization of Mito-Ob mice and the cloning of m-PHB cDNA construct has been reported elsewhere (Ande et al., 2009; Ande et al., 2014). The m-Mito-Ob mice were generated following the same procedure as described previously for Mita-Ob mice (Ande et al., 2014). The animals were given normal chow (LabDiet, St. Louis, Mo.) and water ad libitum. Body weight of m-Mito-Ob and wild-type mice was recorded on a weekly basis after weaning and food intake during 3 to 6 months of age was determined (Ande et al., 2014).

Glucose and Insulin Tolerance Tests

Glucose and insulin tolerance tests in 6 months old Mito-Ob mice; m-Mito-Ob mice, 9-12 months old Mito-Ob mice and their corresponding wild-type littermates were performed as per standard procedures described previously (Nguyen et al., 2011, Endocrinology 152: 2184-2196).

Histology and Immunocytochemistry

Visceral adipose tissue and the liver from 9-12 months old Mito-Ob and wild type littermates as applicable were fixed in buffered formaldehyde (Fisher Scientific, Ottawa, ON) and subsequently dehydrated, embedded in paraffin, and 5 μm sections were stained with hematoxylin-eosin or protein specific antibody for immunohistochemistry (Ande et al., 2014, Diabetes 63: 3431-3437; Nguyen et al., 2011; Nguyen et al., 2015, Endocrinology 156: 462-474).

Lymph node, spleen and tumor tissues from 9-12 months old Mito-Ob, m-Mito-Ob and Wt littermates as applicable were fixed in buffered formaldehyde (Fisher Scientific, Ottawa, ON) and subsequently dehydrated, embedded in paraffin, and 5 μm sections were stained with hematoxylin-eosin (Ande et al., 2014).

Western Immunoblotting

Total liver tissue lysates from Mito-Ob and wild-type mice containing equal amount of proteins (~20 μg/lane) were separated by SDS-PAGE and subsequently analyzed by western immunoblotting using protein specific primary antibody and HRP-conjugated respective secondary antibody as described before (Ande et al., 2014; Nguyen et al., 2011).

Lymph node, spleen and tumor tissue lysates from Mito-Ob, m-Mito-Ob and wild-type mice containing equal amount of proteins (~20 μg/lane) were separated by SDS-PAGE and subsequently analyzed by western immunoblotting using protein specific primary antibody and HRP-conjugated respective secondary antibody as described before (Ande et al., 2014).

Finally, immunodetection was performed using Enhanced Chemiluminescence kit (GE Healthcare, Mississauga, ON).

Adipokines and Hormones Measurements

Adipokines and hormones in mouse serum were measured using mouse Bio-Plex Pro™ Assays Diabetes panel by Bio-Plex 200™ multiplex suspension array systems (Bio-Rad, Hercules, Calif.) as per manufacturer's protocols (Ande et al., 2014).

Apoptosis, Cell Proliferation and Oxidative DNA Damage Measurements

Apoptotic cell death using TUNEL assay (Trevigen, Gaithersburg, Md.) and cell proliferation using anti-Ki67 antibody (Cell Signaling) was measured following the manufacturer's protocol described earlier (Nguyen et al., 2015; Huh et al., 2014). Oxidative DNA damage in the liver tissue was measured using a kit from Biorbyt Ltd. (Cambridgeshire, U.K.) as per the manufacturer's protocol.

Cell Culture, Transfection and Stimulation

RAW264.7 cells were obtained from American Type Culture Collection (ATCC, Manassas, Va.). Cells were cultured and passaged as per ATCC protocol. Cell transfection with vector control and PHB or m-PHB and subsequent stimulation with IGF-I (100 ng/ml for 15 minutes) were performed as described previously (Ande et al., 2009; Venkan et al, 2013).

Chemokine Assays

The serum chemokines were measured using chemokine protein array (R & D Systems) as per the manufacturer's protocol.

Statistical Analysis

All statistical analyses were performed using GraphPad Prism 6. Experimental results are shown as mean±SEM. Two-tailed Student's unpaired t-tests were performed to compare sex-matched Mito-Ob and wild-type littermates or Dunnett's t test in which comparison were made between Mito-Ob mice with and without tumors with a control group. P-values<0.05 were considered significantly different.

The scope of the claims should not be limited by the preferred embodiments set forth in the examples, but should be given the broadest interpretation consistent with the description as a whole.

TABLE 1

Serum hormones and adipokines in m-Mito-Ob and Wt mice at 6-9 months of age. Data are presented as mean ± SEM (n = 5 to 8 in each group).

| | Female | | | | Male | | | |
|---|---|---|---|---|---|---|---|---|
| | Wt | | m-Mito-Ob | | Wt | | m-Mito-Ob | |
| | Fasting | Fed | Fasting | Fed | Fasting | Fed | Fasting | Fed |
| Insulin (ng/ml) | 1.5 ± 0.1 | 4.2 ± 0.6 | 1.6 ± 0.2 | 3.7 ± 0.7 | 1.8 ± 0.2 | 7.2 ± 1.1 | 6.93 ± 0.9** | 14.5 ± 1.7** |
| Ghrelin (ng/ml) | 4.5 ± 0.6 | 2.4 ± 0.4* | 12.3 ± 1.5* | 3.2 ± 0.8 | 4.4 ± 0.3 | 2.2 ± 0.2 | 2.5 ± 0.2*** | 1.1 ± 0.1*** |
| Adiponectin (μg/ml) | 10.1 ± 0.9 | 5.7 ± 0.5 | 13.9 ± 1.6 | 9.1 ± 0.5* | 6.7 ± 0.5 | 4.4 ± 0.4 | 6.5 ± 0.7 | 5.2 ± 0.7 |
| Leptin (ng/ml) | 7.1 ± 1.3 | 4.7 ± 1.1 | 6.0 ± 1.3 | 8.3 ± 1.2 | 8.9 ± 1.6 | 10.2 ± 1.9 | 14.5 ± 1.0* | 15.3 ± 1.2* |

TABLE 1-continued

Serum hormones and adipokines in m-Mito-Ob and Wt mice at 6-9 months of age.
Data are presented as mean ± SEM (n = 5 to 8 in each group).

|  | Female | | | | Male | | | |
| --- | --- | --- | --- | --- | --- | --- | --- | --- |
|  | Wt | | m-Mito-Ob | | Wt | | m-Mito-Ob | |
|  | Fasting | Fed | Fasting | Fed | Fasting | Fed | Fasting | Fed |
| Resistin (ng/ml) | 2.6 ± 0.4 | 1.2 ± 0.1 | 2.3 ± 0.3 | 2.1 ± 0.2 | 2.7 ± 0.5 | 1.7 ± 0.3 | 2.4 ± 0.3 | 2.2 ± 0.5 |

Sex matched fasting vs. fasting or fed vs fed between Wt and m-Mito-Ob.
*$P < 0.05$,
**$P < 0.01$,
***$P < 0.001$ by Student's t test.

TABLE 2

The serum cytokines levels in mice at 9-12 months of age. Data are presented as mean ± SEM (n = 3-4 in each group).

| Cytokine (pg/ml) | Female | | Male | | |
| --- | --- | --- | --- | --- | --- |
|  | Wt | m-Mito-Ob | Wt | m-Mito-Ob | m-Mito-Ob/Tu |
| IL-2 | 29.3 ± 1.92 | 31.5 ± 2.1 | 24.7 ± 1.81 | 22.8 ± 1.14 | 12.4 ± 0.92**,+ |
| IL-6 | 13.6 ± 1.16 | 15.7 ± 1.35 | 9.3 ± 0.97 | 11.9 ± 0.93* | 6.7 ± 0.72*,++ |
| IL-10 | 258.4 ± 15.87 | 417.9 ± 23.71*** | 253.3 ± 18.54 | 145.6 ± 11.37** | 112.5 ± 9.41***,+ |
| IL-12 | 451.7 ± 3.45 | 579.3 ± 10.61* | 399.4 ± 14.37 | 317.2 ± 13.19 | 217.9 ± 8.84**,+ |
| INF-γ | 84.1 ± 6.91 | 112.3 ± 8.93* | 87.4 ± 7.36 | 68.7 ± 8.81 | 50.8 ± 7.26*,+ |
| TNF-α | 3146 ± 15.21 | 4020 ± 22.19* | 3068 ± 13.95 | 2364 ± 18.46* | 1742 ± 17.93**,+ |

Sex matched Wt vs m-Mito-Ob or m-Mito-Ob/Tu *$p < 0.05$, $p < 0.01$, *$p < 0.001$, and m-Mito-Ob vs m-Mito-Ob/Tu +$p < 0.05$, ++$p < 0.01$ by Student's t test or Dunnett's t test.

The invention claimed is:

1. A male transgenic mouse whose genome comprises an exogenous nucleic acid construct comprising adipocyte protein 2 (aP2) promoter operably linked to a gene encoding Y114F mutant prohibitin, wherein expression of said gene results in said male transgenic mouse developing histiocytosis and lymphadenopathy as compared to a wild-type male mouse of the same strain.

2. The male transgenic mouse according to claim 1 wherein the Y114F mutant prohibitin gene consists of the amino acid sequence as set forth in SEQ ID No:3.

3. The male transgenic mouse according to claim 1 wherein the aP2 promoter consists of the nucleotide sequence as set forth in SEQ ID No:1.

4. A method of determining if a compound of interest reduces severity of histiocytosis and/or lymphadenopathy in a male transgenic mouse comprising:

producing the male transgenic mouse according to claim 1 to approximately at least 3 months of age;

administering a compound of interest to the male transgenic mouse; and determining if the compound of interest delays onset or reduces severity of histiocytosis and/or lymphadenopathy in the male transgenic mouse.

* * * * *